(12) United States Patent
Vigo et al.

(10) Patent No.: US 9,757,398 B2
(45) Date of Patent: Sep. 12, 2017

(54) PREVENTION AND TREATMENT OF ALZHEIMER'S DISEASE BY AMYLOID BETA PEPTIDE AND SPHIN-GOSINE-1-PHOSPHATE

(75) Inventors: Carmen Vigo, Mountain View, CA (US); Ramon Cacabelos, Bergondo (ES)

(73) Assignee: EUROESPES BIOTECNNOLOGIA, S.L., Bergondo (Coruna) (ES)

( * ) Notice: Subject to any disclaimer, the term of this patent is extended or adjusted under 35 U.S.C. 154(b) by 878 days.

(21) Appl. No.: 13/703,166

(22) PCT Filed: Feb. 18, 2011

(86) PCT No.: PCT/US2011/000305
§ 371 (c)(1),
(2), (4) Date: Apr. 9, 2013

(87) PCT Pub. No.: WO2011/102901
PCT Pub. Date: Aug. 25, 2011

(65) Prior Publication Data
US 2013/0202680 A1    Aug. 8, 2013

Related U.S. Application Data

(60) Provisional application No. 61/306,452, filed on Feb. 20, 2010.

(51) Int. Cl.
A61K 6/00    (2006.01)
A61K 38/16    (2006.01)
(Continued)

(52) U.S. Cl.
CPC .......... *A61K 31/661* (2013.01); *A61K 9/127* (2013.01); *A61K 31/133* (2013.01);
(Continued)

(58) Field of Classification Search
None
See application file for complete search history.

(56) References Cited

U.S. PATENT DOCUMENTS

2005/0037063 A1*   2/2005   Bolton ................... A61K 9/127
                                                            424/450
2005/0169979 A1    8/2005   Michaeli et al.
(Continued)

OTHER PUBLICATIONS

Malaplate-Armand et al., Soluble oligomers of amyloid-B peptide induce neuronal apoptosis by activating a cPLA2-dependent sphingomyelinase-ceramide pathway. Neurobiology of Disease 23 (2006) 178-189.*

(Continued)

*Primary Examiner* — Jeffrey Stucker
*Assistant Examiner* — Aurora M Fontainhas
(74) *Attorney, Agent, or Firm* — Sughrue Mion, PLLC

(57) ABSTRACT

The invention provides compositions and methods for treatment of Alzheimer's disease. Such methods entail administering agents that induce a beneficial immune and therapeutic response against an amyloid deposit in the patient. The methods are particularly useful for prophylactic and therapeutic treatment of Alzheimer's disease. In certain preferred embodiments of such methods, a preferred agent is amyloid beta peptide in combination with Sphingosine-1-phosphate, preferably delivered in certain embodiments in a liposomal formulation.

20 Claims, 20 Drawing Sheets
(17 of 20 Drawing Sheet(s) Filed in Color)

(51) Int. Cl.
- *A61K 8/18* (2006.01)
- *C12N 15/88* (2006.01)
- *G01N 33/92* (2006.01)
- *G01N 33/15* (2006.01)
- *A61K 31/661* (2006.01)
- *A61K 9/127* (2006.01)
- *A61K 31/133* (2006.01)
- *A61K 38/17* (2006.01)
- *A61K 45/06* (2006.01)
- *A61K 39/00* (2006.01)

(52) U.S. Cl.
CPC ...... *A61K 38/1709* (2013.01); *A61K 39/0007* (2013.01); *A61K 45/06* (2013.01)

(56) References Cited

U.S. PATENT DOCUMENTS

2005/0266502 A1 12/2005 Merchiers et al.
2009/0191231 A1 7/2009 Schenk et al.

OTHER PUBLICATIONS

Yan et al., "Protection against beta-amyloid peptide toxicity in vivo with long-term administration of ferulic acid", Br. J. Pharmacol., vol. 133, No. 1; pp. 89-96 (2001).

International Search Report mailed May 5, 2011, which issued in corresponding International Application No. PCT/US2011/000305.

Written Opinion of the International Searching Authority mailed May 5, 2011, which issued in corresponding International Application No. PCT/US2011/000305.

International Preliminary Report on Patentability mailed Aug. 21, 2012, which issued in corresponding International Application No. PCT/US2011/000305.

* cited by examiner

Antobody Titers in BA-SIP Liposome Vaccinated Transgenic Mice

FIGURE 2

Glia (GFAP) Immunochemistry
(Phase I)

Lymphocytes B CD45 Immunochemistry
(Phase I)

Lymphocytes T CD3 Immunochemistry
(Phase I)

Apoptosis Immunochemistry
(Phase I)

PREVENTION AND TREATMENT OF ALZHEIMER'S DISEASE BY AMYLOID BETA PEPTIDE AND SPHIN-GOSINE-1-PHOSPHATE

CROSS REFERENCE TO PRIOR APPLICATIONS

This is a U.S. National Phase application under 35 U.S.C. §371 of International Patent Application No. PCT/US2011/000305, filed Feb. 18, 2011, and claims the benefit of Provisional Application No. 61/306,452, filed Feb. 20, 2010 both of which are incorporated by reference herein in their entirety. The International Application published in English on Aug. 25, 2011 as WO 2011/102901 under PCT Article 21(2).

TECHNICAL FIELD AND INDUSTRIAL APPLICABILITY

This application relates to the prevention and treatment of neurological conditions.

BACKGROUND ART

Alzheimer's disease (AD) is a progressive neurodegenerative disease resulting in senile dementia. AD is the most common form of dementia. See generally Selkoe, TINS 16, 403-409 (1993); Hardy et al., WO 92/13069; Selkoe, J. Neuropathol. Exp. Neurol. 53, 438-447 (1994); Duff et al., Nature 373, 476-477 (1995); Games et al., Nature 373, 523 (1995). In general, the disease falls into two categories: late onset, which occurs in old age (65+ years) and early onset, which develops well before the senile period, i.e., between 35 and 60 years. In both types of disease, the pathology is the same but the A. beta peptide abnormalities tend to be more severe and widespread in cases where the AD symptoms begin at an earlier age, sometimes as early as the fourth decade of life. The disease is characterized by two types of lesions in the brain, senile plaques, composed mainly by aggregated long form of beta amyloid peptide, 39-42 amino acids, and neurofibrillary tangles, composed of phosphorylated cytoskeletal protein named tau. Senile plaques are areas of disorganized neuropil up to 150 μn across with extracellular amyloid deposits at the center visible by microscopic analysis of sections of brain tissue. Neurofibrillary tangles are intracellular deposits of tau protein consisting of two filaments twisted about each other in pairs.

A. beta peptide (also referred to herein as A. beta, Aβ, Aβ peptide, or amyloid beta peptide) is an internal fragment of 39-43 amino acids of a precursor protein termed amyloid precursor protein (APP). Several mutations within the APP protein have been correlated with the presence of Alzheimer's disease. See, e.g., Goate et al., Nature 349, 704) (1991) (valine$^{717}$ to isoleucine); Chartier Harlan et al. Nature 353, 844 (1991)) (valine$^{717}$ to glycine); Murrell et al., Science 254, 97 (1991) (valine$^{717}$ to phenylalanine); Mullan et al., Nature Genet. 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to A. beta, particularly processing of APP to increased amounts of the long form of A. beta (i.e., A. beta1-42 and A. beta1-43). Mutations in other genes, such as the presenilin genes, PS1 and PS2, are thought indirectly to affect processing of APP to generate increased amounts of long form A. beta (see Hardy, TINS 20, 154 (1997)). These observations indicate that A. beta, and particularly its long form, is at least one of the causative elements in Alzheimer's disease.

In early discoveries, McMichael, EP 526,511, proposed administration of homeopathic dosages (less than or equal to 10.sup.-2 mg/day) of A. beta to patients with pre-established AD. In a typical human with about 5 liters of plasma, even the upper limit of this dosage would typically be expected to generate a concentration of no more than 2 pg/ml. The normal concentration of A. beta in human plasma is typically in the range of 50-200 pg/ml (Seubert, Vigo-Pelfrey et al., Nature 359, 325-327 (1992)).

Schenk et al, Nature, 1999 demonstrated that administration of the aggregated form of beta amyloid peptide with 42 amino acids reversed the AD pathology in the brain of transgenic mice. Their similar experiments later conducted in humans however, resulted in an encephalitic-like inflammatory reaction in the brain of these patients resulting in death in some of them. This inflammatory reaction has been attributed to a Th2 immunoreaction. The clinical studies were immediately stopped and other forms of immunization are being tested, particularly using various kinds of antibodies that recognize particular epitopes of the amyloid beta peptide.

Sphingosine-1-phosphate (S1P) is present in blood plasma and is one of the most potent growth factors displaying proangiogenic properties, (Pilorget et al, Journal of Cerebral Blood Flow & Metabolism, 2005). S1P has been shown to act as an intracellular and extracellular messenger in the nervous system (Anelli et al, J. of Neurochemistry, 2005), to control proliferation, survival, differentiation and prevent apoptosis in neural cells, thereby regulating neural signaling and function (Colombaioni, Garcia-Gil, Brain Research Reviews, 2004, Saba and Hla, Circulation Research, 2007). S1P also controls migration of neuronal stem cells toward a site of spinal cord injury, thereby suggesting that S1P has a therapeutic potential as a regenerative agent in the nervous system (Kimura et al, Stem Cells, 2007).

From all these observations, we have concluded that S1P in combination with A. beta peptide administered in a liposomal formulation or even with other non-liposomal adjuvant would improve the therapeutic or prophylactic effects of amyloid beta peptide seen before, while preventing apoptosis and inflammation and inducing neuronal repair and survival. The liposomal formulation used as adjuvant, not only incorporates S1P and A. beta peptide into the bilayer, but also preserves the structure of A. beta peptide which in combination with S1P should prevent the inflammatory reactions observed in previous AD vaccines using A. beta peptide alone.

Thus, in certain preferred embodiments the present invention is directed to treatment of Alzheimer's and other amyloidogenic diseases by administration of A. beta peptide 42 and S1P integrated in a liposomal configuration, herein called EB101, to a patient under conditions that generate a beneficial immune response in the patient while preventing inflammation and stimulating neuronal repair and regeneration. The invention thus fulfills a longstanding need for therapeutic regimes for preventing or ameliorating the neuropathology of AD and other amyloidogenic diseases.

DISCLOSURE OF THE INVENTION

In one embodiment, the invention provides methods of preventing or treating a disease characterized by amyloid deposition in a patient with AD or other pathology related to AD-like Down syndrome. Such methods entail inducing an immune response against a peptide component of an amyloid deposit in the patient while preventing an inflammatory response and inducing neuronal regeneration and repair by using S1P in combination with the immunogen, A. beta peptide with 42 amino acids. In AD patients, the amyloid deposit is aggregated or non-aggregated A. beta peptide. In some embodiment methods of this invention, the patient is asymptomatic. In some embodiment methods, the patient is younger than 50 years of age. In some embodiment methods, the patient has inherited risk factors indicating susceptibility to Alzheimer's disease. Such risk factors include variant alleles in presenilin gene PS1 or PS2 and variant forms of APP. In other embodiment methods, the patient has no known risk factors for Alzheimer's disease.

For treatment of patients suffering from Alzheimer's disease, one embodiment of this invention provides a treatment regime that entails administering a dose of A. beta peptide 42 and S1P to the patient to induce the immune response to A. beta peptide 42 in conjunction with an antiapoptotic, neuronal regenerative agent, S1P. In some embodiment methods, the A. beta peptide and S1P are administered with a liposomal adjuvant that enhances the immune response to the A. beta peptide. In some embodiments, the preferred dose of A. beta peptide administered to the patient is typically at least 10 or 100 μg and the amount of S1P is 0.1 to 10 μg, if administered in the liposomal adjuvant.

In some embodiment methods, the A. beta peptide is A. beta1-42 with S1P. In some embodiment methods, the A. beta peptide is administered in aggregated form with S1P. In other embodiment methods the A beta peptide is administered in non-aggregated form in combination with S1P.

In other embodiment methods, the A. beta peptide is administered in dissociated form with S1P. In some methods, the therapeutic agent is an effective dose of a nucleic acid encoding A. beta or an active fragment or derivative thereof in combination with S1P. The nucleic acid encoding A. beta or fragment thereof is expressed in the patient to produce A. beta or the active fragment thereof, which induces the immune response. In some such embodiment methods, the nucleic acid and S1P are administered through the skin, optionally via a patch. In some methods, a therapeutic agent is identified by screening a library of compounds to identify a compound reactive with antibodies to A. beta and S1P, and administering the compounds to the patient to induce the immune response to A. beta In some embodiment methods, the immune response is directed to aggregated A. beta peptide without being directed to dissociated A. beta peptide administered with S1P.

The therapeutic agents are typically administered orally, intranasally, intradermally, subcutaneously, intramuscularly, topically or intravenously. In some embodiment methods, the patient is monitored followed administration to assess the immune response. If the monitoring indicates a reduction of the immune response over time, the patient can be given one or more further doses of the agent.

In other embodiments of this invention, the invention provides pharmaceutical compositions comprising A. beta in combination with S1P and an excipient suitable for oral and other routes of administration. Some invention embodiments also provide pharmaceutical compositions comprising an agent effective to induce an immunogenic response against A. beta in combination with S1P in a patient, and a liposomal adjuvant. In certain embodiments, the adjuvant for this therapeutic combination could be of non-liposomal nature.

In some such compositions, the agent is A. beta or an active fragment thereof in combination with S1P. In some embodiment compositions, the adjuvant comprises liposomes. In some compositions a lipid can be pegylated, in some compositions S1P can be pegylated. In some compositions A. beta is pegylated and in some methods A. beta is bound to S1P. In some embodiment compositions, the adjuvant is of a micellar type. In some cases the adjuvant is non-liposomal.

The invention further provides methods of preventing or treating Alzheimer's disease. In some embodiments of such methods, an effective dose of A. beta peptide and S1P are administered to a patient. Some embodiments of this invention further provide for the use of A. beta and S1P, or an antibody thereto, in the manufacture of a medicament for prevention or treatment of Alzheimer's disease.

Other embodiment methods of monitoring Alzheimer's disease or susceptibility thereto in a patient, comprise detecting an immune response against A. beta peptide in a sample from the patient. In some such embodiment methods, the patient is being administered an agent effective to treat or prevent Alzheimer's disease, and the level of the response determines the future treatment regime of the patient.

In some embodiments of this invention, other methods are provided for assessing efficacy of an Alzheimer's treatment method in a patient, comprising a value for an amount of antibody specific for A. beta peptide in tissue samples from a patient who has been treated with A. beta peptide and S1P. In certain embodiments, the value may be compared with a control value determined from a population of patient experiencing amelioration of or freedom from, symptoms of Alzheimer's disease due to treatment with the agent with a value in the patient in such embodiments at least equal to the control value indicates a positive response to treatment.

The invention further provides diagnostic kits for performing the above embodiment methods. Such kits typically include a reagent that specifically binds to antibodies to A. beta or which stimulates proliferation of T-cells reactive with A. beta. Some embodiments of this invention further provide therapeutic compositions comprising a dosage of an A. beta peptide greater than 10 μg and a dosage of S1P greater than 0.1 μg and a pharmaceutically acceptable adjuvant, such dosages suitable for administration in a regime effective to induce an immune response to A. beta, said immune response comprising production of antibodies to the A. beta peptide.

In certain preferred embodiments of the present invention, we combine the use of a biologically active lipid, Sphingosine-1-phosphate (S1P) with A. beta peptide, with a liposomal adjuvant.

In other embodiments, S1P and A. beta peptide are delivered to a patient formulated in a non-liposomal adjuvant, such as but not limited to alum, 3 De-O-acylated monophosphoryl lipid A (MPL) or QS21, M-CSF, or GM-CSF.

BRIEF DESCRIPTION OF DRAWINGS

The patent or application file contains at least one drawing executed in color. Copies of this patent or patent application publication with other color drawing(s) will be provided by the Office upon request and payment of the necessary fee.

FIG. 2 shows five out of six EB101 liposome vaccinated transgenic mice showed different titers of specific IgG antibodies. One out of six mice showed very high antibody titers (>1/50000) suggesting a very good response to immunization. Each bar represents the mean of triplicate wells±SD.

BEST MODE FOR CARRYING OUT THE INVENTION

Figure 1:
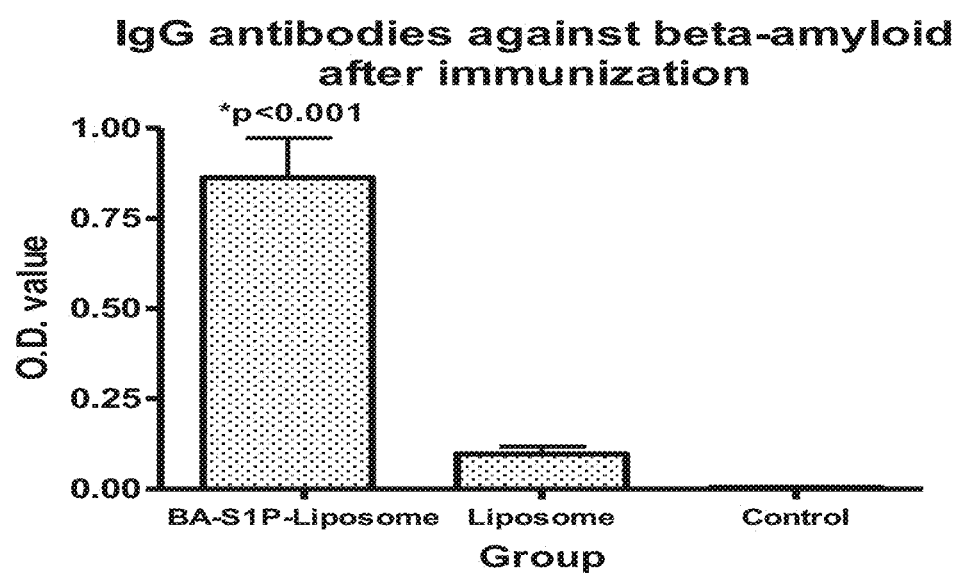
FIG. 1. shows the presence of anti β-amyloid in the sera of vaccinated and control transgenic mice. Each bar represents the mean±SD in each group.

The invention provides pharmaceutical compositions and methods for prophylactic and therapeutic treatment of diseases characterized by accumulation of amyloid deposits.

Amyloid deposits comprise a peptide aggregated to an insoluble mass. The nature of the peptide varies in different diseases but in most cases, the aggregate has a .beta.-pleated sheet structure and stains with Congo Red dye. Diseases characterized by amyloid deposits include Alzheimer's disease (AD), both late and early onset. In both diseases, the amyloid deposit comprises a peptide termed A. beta, which accumulates in the brain of affected individuals. Examples of some other diseases characterized by amyloid deposits are amyloidosis, Dawn syndrome, hereditary Icelandic syndrome, multiple myeloma, and spongiform encephalopathies, including mad cow disease, Creutzfeldt Jakob disease, sheep scrapie, and mink spongiform encephalopathy (see Weissmann et al., Curr. Opin. Neurobiol. 7, 695-700 (1997); Smits et al., Veterinary Quarterly 19, 101-105 (1997); Nathanson et al., Am. J. Epidemiol. 145, 959-969 (1997)). The peptides forming the aggregates in these diseases are serum amyloid A, cystanin C, IgG kappa light chain respectively for the first three, and prion protein for the others.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions that are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identify and sequence similarity is the BLAST algorithm, which is described in Altschul et al., J. Mol. Biol. 215:403-410 (1990). Software for performing BLAST analyses is publicly available through the National Center or Biotechnology Information (http://www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89, 10915 (1989)).

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gin, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Therapeutic agents of the invention are typically substantially pure. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

Specific binding between two entities means an affinity of at least $10^6$, $10^7$, $10^8$, $10^9$ $M^{-1}$, or $10^{10}$ $M^{-1}$. Affinities greater than $10^8$ $M^{-1}$ are preferred.

The term "antibody" is used to include intact antibodies and binding fragments thereof. Typically, fragments compete with the intact antibody from which they were derived for specific binding to an antigen. Optionally, antibodies or binding fragments thereof, can be chemically conjugated to, or expressed as, fusion proteins with other proteins.

$APP^{695}$, $APP^{751}$, $APP^{770}$ refer, respectively, to the 695, 751, and 770 amino acid residue long polypeptides encoded by the human APP gene. See Kang et al., Nature 325, 773 (1987); Ponte et al., Nature 331, 525 (1988); and Kitaguchi et al., Nature 331, 530 (1988). Amino acids within the human amyloid precursor protein (APP) are assigned numbers according to the sequence of the APP770 isoform. Terms such as A. beta39, A. beta40, A. beta41, A. beta42 and A. beta43 refer to an A. beta peptide containing amino acid residues 1-39, 1-40, 1-41, 1-42 and 1-43.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4.sup.+ T helper cells and/or CD8.sup.+cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4.sup.+ T cells) or CTL (cytotoxic T lymphocyte) assays (see Burke, supra; Tigges, supra). The relative contributions of humoral and cellular responses to the protective or therapeutic effect of an immunogen can be distinguished by separately isolating IgG and T-cells from an immunized syngeneic animal and measuring protective or therapeutic effect in a second subject.

An "immunogenic agent" or "immunogen" is capable of inducing an immunological response against itself on administration to a patient, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Disaggregated or monomeric A. beta means soluble, monomeric peptide units of A. beta. One method to prepare monomeric A. beta is to dissolve lyophilized peptide in neat DMSO with sonication. The resulting solution is centrifuged to remove any nonsoluble particulates. Aggregated A. beta is a mixture of oligomers in which the monomeric units are held together by noncovalent bonds.

Compositions or methods "comprising" one or more recited elements may include other elements not specifically recited. For example, a composition that comprises A. beta peptide encompasses both an isolated A. beta peptide and A. beta peptide as a component of a larger polypeptide sequence.

Therapeutic Agents
1. Alzheimer's Disease

Therapeutic agents for use in the present invention induce an immune response against A. beta peptide but not against S1P, administered in sub immune reactive amounts. These agents include A. beta peptide itself and variants thereof, analogs and mimetics of A. beta peptide that induce and/or cross-react with antibodies to A. beta. peptide, and antibodies or T-cells reactive with A. beta peptide in combination with S1P. Induction of an immune response can be active as when an immunogen is administered to induce antibodies or T-cells reactive with A. beta in a patient, or passive, as when an antibody is administered that itself binds to A. beta in the patient, in combination with S1P to prevent inflammatory reactions.

A. beta, also known as .beta.-amyloid peptide, Aβ or A4 peptide (see U.S. Pat. No. 4,666,829; Glenner & Wong, Biochem. Biophys. Res. Commun. 120, 1131 (1984)), is a peptide of 39-43 amino acids, which is the principal component of characteristic plaques of Alzheimer's disease. A. beta is generated by processing of a larger protein APP by two enzymes, termed .beta. and .gamma. secretases (see Hardy, TINS 20, 154 (1997)). Known mutations in APP associated with Alzheimer's disease occur proximate to the site of .beta. or .gamma. secretase, or within A. beta. For example, position 717 is proximate to the site of .gamma.-secretase cleavage of APP in its processing to A. beta, and positions 670/671 are proximate to the site of .beta.-secretase cleavage. It is believed that the mutations cause AD disease by interacting with the cleavage reactions by which A. beta is formed so as to increase the amount of the 42/43 amino acid form of A. beta generated.

A. beta has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes A. beta to generate an immune response in excess of that of other antigens.

The therapeutic agent used in the claimed methods can be any of the naturally occurring forms of A. beta peptide, and particularly the human forms (i.e., A. beta39, A. beta40, A. beta41, A. beta or A. beta43) in combination with S1P. The sequences of these peptides and their relationship to the APP precursor are illustrated by Hardy et al., TINS 20, 155-158 (1997), the disclosure of which is hereby incorporated by reference.

A. beta41, A. beta40 and A. beta39 differ from A. beta42 by the omission of Ala, Ala-Ile, and Ala-Ile-Val respectively from the C-terminal end. A. beta43 differs from A. beta42 by the presence of a threonine residue at the C-terminus. The therapeutic agent can also be an active fragment or analog of a natural A. beta peptide that contains an epitope that induces a similar protective or therapeutic immune response on administration to a human in combination with S1P. Immunogenic fragments typically have a sequence of at least 3, 5, 6, 10 or 20 contiguous amino acids from a natural peptide. Immunogenic fragments include A. beta1-5, 1-6, 1-12, 13-28, 17-28, 25-25, 35-40 and 35-42. Fragments from the N-terminal half of A. beta are preferred in some methods. Analogs include allelic, species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are .alpha., .alpha.-disubstituted amino acids, N-alkyl amino acids, lactic acid, 4-hydroxyproline, .gamma.-carboxyglutamate, .epsilon.-N,N,N-trimethyllysine, .epsilon.-N-acetyllysine, O-phosphoserine, N-acetylserine, N-formylmethionine, 3-methylhistidine, 5-hydroxylysine, .omega.-N-methylarginine. Fragments and analogs can be screened for prophylactic or therapeutic efficacy in transgenic animal models as described below.

A. beta, its fragments, analogs and other amyloidogenic peptides can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., Molecular Cloning: A Laboratory Manual (C.S.H.P. Press, NY 2d ed., 1989). Some forms of A. beta peptide are also available commercially (e.g., American Peptides Company, Inc., Sunnyvale, Calif. and California Peptide Research, Inc. Napa, Calif.).

Therapeutic agents also include longer polypeptides that include, for example, an A. beta peptide, active fragment or analog together with other amino acids always administered with S1P. For example, A. beta peptide can be present as intact APP protein or a segment thereof, such as the C-100 fragment that begins at the N-terminus of A. beta and continues to the end of APP. Such polypeptides can be screened for prophylactic or therapeutic efficacy in animal models as described below. The A. beta peptide, analog, active fragment or other polypeptide can be administered in associated form (i.e., as an amyloid peptide) or in dissociated form. Therapeutic agents also include multimers of monomeric immunogenic agents.

In a further variation, an immunogenic peptide, such as A. beta, in combination with S1P can be presented as a viral or bacterial vaccine. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacterium so that the peptide is displayed. Viruses or bacteria used in such methods should be nonpathogenic or attenuated. Suitable viruses include adenovirus, HSV, vaccinia and fowl pox. Fusion of an immunogenic peptide to HBsAg of HBV is particularly suitable. Therapeutic agents also include peptides and other compounds that do not necessarily have a significant amino acid sequence similarity with A. beta but nevertheless serve as mimetics of A. beta and induce a similar immune response. For example, any peptides and proteins forming .beta.-pleated sheets can be screened for suitability. Anti-idiotypic antibodies against monoclonal antibodies to A. beta or other amyloidogenic peptides can also be used in combination with S1P. Such anti-Id antibodies mimic the antigen and generate an immune response to it (see Essential Immunology (Roit ed., Blackwell Scientific Publications, Palo Alto, 6th ed.), p. 181).

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates combined with S1P. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for A. beta or other amyloidogenic peptides. For example, initial screens can be performed with any polyclonal sera or monoclonal antibody to A. beta or other amyloidogenic peptide. Compounds identified by such screens are then further analyzed for capacity to induce antibodies or reactive lymphocytes to A. beta or other amyloidogenic peptide. For example, multiple dilutions of sera can be tested on microtiter plates that have been precoated with A. beta peptide and a standard ELISA can be performed to test for reactive antibodies to A. beta. Compounds can then be tested for prophylactic and therapeutic efficacy in transgenic animals predisposed to an amyloidogenic disease, as described in the Examples. Such animals include, for example, mice bearing a 717 mutation of APP described by Games et al., supra, and mice bearing a Swedish mutation of APP such as described by McConlogue et al., U.S. Pat. No. 5,612,486 and Hsiao et al., Science 274, 99 (1996); Staufenbiel et al., Proc. Natl. Acad. Sci. USA 94, 13287-13292 (1997); Sturchler-Pierrat et al., Proc. Natl. Acad. Sci. USA 94, 13287-13292 (1997); Borchelt et al., Neuron 19, 939-945 (1997)). The same screening approach can be used on other potential agents such as fragments of A. beta, analogs of A. beta and longer peptides including A. beta, described above in combination with S1P.

Therapeutic agents of the invention also include antibodies that specifically bind to A. beta combined with S1P. Such antibodies can be monoclonal or polyclonal. Some such antibodies bind specifically to the aggregated form of A. beta without binding to the dissociated form. Some bind specifically to the dissociated form without binding to the aggregated form. Some bind to both aggregated and dissociated forms. The production of non-human monoclonal antibodies, e.g., murine or rat, can be accomplished by, for example, immunizing the animal with A. beta. See Harlow & Lane, Antibodies, A Laboratory Manual (CSHP NY, 1988) (incorporated by reference for all purposes). Such an immunogen can be obtained from a natural source, by peptides synthesis or by recombinant expression.

Humanized forms of mouse antibodies can be generated by linking the CDR regions of non-human antibodies to human constant regions by recombinant DNA techniques combined with S1P. See Queen et al., Proc. Natl. Acad Sci. USA 86, 10029-10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to A. beta, or fragments thereof. Human antibodies against A. beta can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using A. beta or other amyloid peptide as an affinity reagent. Administration is always in combination with S1P.

Human or humanized antibodies can be designed to have IgG, IgD, IgA and IgE constant region, and any isotype, including IgG1, IgG2, IgG3 and IgG4. Antibodies can be expressed as tetramers containing two light and two heavy chains, as separate heavy chains, light chains, as Fab, Fab'

F(ab').sub.2, and Fv, or as single chain antibodies in which heavy and light chain variable domains are linked through a spacer.

Therapeutic agents for use in the present methods also include T-cells that bind to A. beta peptide. For example, T-cells can be activated against A. beta peptide by expressing a human MHC class I gene and a human .beta.-2-microglobulin gene from an insect cell line, whereby an empty complex is formed on the surface of the cells and can bind to A. beta peptide. T-cells contacted with the cell line become specifically activated against the peptide. See Peterson et al., U.S. Pat. No. 5,314,813. Insect cell lines expressing an MHC class II antigen can similarly be used to activate CD4 T cells. Administration is always in combination with S1P.

2. Other Diseases

The same or analogous principles determine production of therapeutic agents for treatment of other amyloidogenic diseases. In general, the agents noted above for use in treatment of Alzheimer's disease can also be used for treatment early onset Alzheimer's disease associated with Down's syndrome. In mad cow disease, prion peptide, active fragments, and analogs, and antibodies to prion peptide are used with or in place of A. beta peptide, active fragments, analogs and antibodies to A. beta peptide in treatment of Alzheimer's disease. In treatment of multiple myeloma, IgG light chain and analogs and antibodies thereto are used, and so forth in other diseases.

Carrier Proteins

Some agents for inducing an immune response to amyloid beta peptide or fragment, in combination with S1P, contain the appropriate epitope for inducing an immune response against amyloid deposits but are too small to be immunogenic. In this situation, a peptide immunogen can be linked to a suitable carrier to help elicit an immune response. Such formulations are within the scope of the compositions and methods claimed herein. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, E. coli, cholera, or H. pylori, or an attenuated toxin derivative. Other carriers for stimulating or enhancing an immune response include cytokines such as IL-1, IL-1.alpha. and .beta. peptides, IL-2, .gamma INF, IL-10, GM-CSF, and chemokines, such as M1P1.alpha. and .beta. and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the .epsilon.-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimidomethyl)cyclohexane-1-carboxylic acid. The carboxyl groups can be activated by combining them with succinimide or 1-hydroxyl-2-nitro-4-sulfonic acid, sodium salt.

Immunogenic peptides can also be expressed as fusion proteins with carriers. The immunogenic peptide can be linked at the amino terminus, the carboxyl terminus, or internally to the carrier. Optionally, multiple repeats of the immunogenic peptide can be present in the fusion protein.

Nucleic Acid Encoding Immunogens

Immune responses against amyloid deposits can also be induced by administration of nucleic acids encoding A. beta peptide or other peptide immunogens in combination with S1P. Such nucleic acids can be DNA or RNA. A nucleic acid segment encoding the immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector.

A number of viral vector systems are available including retroviral systems (see, e.g., Lawrie and Tumin, Cur. Opin. Genet. Develop. 3, 102-109 (1993)); adenoviral vectors (see, e.g., Bett et al., J. Virol. 67, 5911 (1993)); adeno-associated virus vectors (see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), and papillomaviruses (Ohe et al., Human Gene Therapy 6, 325-333 (1995); Woo et al., WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833 and 5,283,185. Vectors and DNA encoding an immunogen can also be adsorbed to or associated with particulate carriers, examples of which include polymethyl methacrylate polymers and polylactides and poly(lactide-co-glycolides), see, e.g., McGee et al., J. Micro Encap. (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton, Wis. is suitable. Alternatively, naked DNA can pass through skin into the blood stream simply by spotting the DNA onto skin with chemical or mechanical irritation (see WO 95/05853).

In a further variation, vectors encoding immunogens in combination with S1P can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Patients Amenable to Treatment

Patients amenable to treatment include individuals at risk of disease but not showing symptoms, as well as patients presently showing symptoms. In the case of Alzheimer's disease, virtually anyone is at risk of suffering from Alzheimer's disease if he or she lives long enough. Therefore, the present methods can be administered prophylactically to the general population without any assessment of the risk of the subject patient, and without assessment of the presence or absence of amyloid beta deposits. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and A. beta42 levels. Elevated tau and decreased A. beta42 levels signify the presence of AD. Individuals suffering from Alzheimer's disease can also be diagnosed by MMSE or ADRDA criteria as discussed in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to the therapeutic agent (e.g., A. beta peptide) over time. If the response falls, a booster dosage is indicated. In the case of potential Down's syndrome patients, treatment can begin antenatally by administering therapeutic agent to the mother or shortly after birth.

Treatment Regimes

In prophylactic applications, pharmaceutical compositions or medicaments are administered to a patient susceptible to, or otherwise at risk of, a particular disease in an amount sufficient to eliminate or reduce the risk or delay the outset of the disease. In therapeutic applications, compositions or medicaments are administered to a patient suspected of or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human, but in some diseases, such as mad cow disease, the patient can be a nonhuman mammal, such as a bovine. Treatment dosages need to be titrated to optimize safety and efficacy. The amount of immunogen depends on whether adjuvant is also administered, with higher dosages being required in the absence of adjuvant. The amount of an A. beta immunogen for administration sometimes varies from 100 µg-5000 µg and S1P from 0.01 µg to 50 µg per patient and more usually from 100 µg-1000 µg A. beta and 1 µg to 50 µg S1P per injection for human administration. Occasionally, a higher dose of 1-2 mg per injection is used. Typically about 100, 200, 500, 700 or 1000 µg of A. beta and 0.1, 1.0, 5.0 or 10 µg S1P is used for each human injection. In certain preferred embodiments of this invention, the dose of the A. beta peptide administered to the patient is between 20 and 700 µg and the dose of S1P is between 2 and 70 µg. In other embodiment, the dose of the A. beta peptide administered to the patient is between 10 and 50 µg and the dose of S1P is between 1 and 50 µg. In yet other embodiments, the dose of the A. beta peptide administered to the patient is approximately 100 µg and the dose of S1P is approximately 6 µg.

The timing of injections can vary significantly from once a day, to once a year, to once a decade. On any given day that a dosage of immunogen is given, the dosage is greater than 1 µg/patient and usually greater than 100 µg/patient if adjuvant is also administered, and greater than 10 µg/patient and usually greater than 100 µg/patient in the absence of adjuvant. A typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on an irregular basis as indicated by monitoring of immune response. For passive immunization with an antibody, the dosage ranges from about 0.0001 to 100 mg/kg, and more usually 0.01 to 5 mg/kg of the host body weight. Doses for nucleic acids encoding immunogens range from about 10 ng to 1 g, 100 ng to 100 mg, 1 µg to 10 mg, or 30-300 µg DNA per patient. Doses for infectious viral vectors vary from 10-10.sup.9, or more, virions per dose.

Agents for inducing an immune response can be administered by parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intraarterial, intracranial, or intradermal injections are also effective in generating an immune response. In some methods, agents are injected directly into a particular tissue where deposits have accumulated.

Agents of the invention can optionally be administered in combination with other agents that are at least partly effective in treatment of amyloidogenic disease. In the case of Alzheimer's and Down's syndrome, in which amyloid deposits occur in the brain, agents of the invention can also be administered in conjunction with other agents that increase passage of the agents of the invention across the blood-brain barrier.

Immunogenic agents of the invention, such as peptides combined with S1P, are administered with a liposomal adjuvant. The preferred lipid composition is phosphatidyl choline:phosphatidyl glycerol:cholesterol in a molar ratio of 0.3:0.3:0.39. Other phospholipids could be used with or without cholesterol. A variety of other non-liposomal adjuvants can be used in combination with S1P to elicit an immune response to A. beta peptide. Preferred adjuvants augment the intrinsic response to an immunogen without causing conformational changes in the immunogen that affect the qualitative form of the response. Preferred adjuvants include alum, 3 De-O-acylated monophosphoryl lipid A (MPL) (see GB 2220211). QS21 is a triterpene glycoside or saponin isolated from the bark of the Quillaja *Saponaria Molina* tree found in South America (see Kensil et al., in Vaccine Design: The Subunit and Adjuvant Approach (eds. Powell & Newman, Plenum Press, NY, 1995); U.S. Pat. No. 5,057,540). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Alternatively, A. beta can be coupled to an adjuvant. For example, a lipopeptide version of A. beta can be prepared by coupling palmitic acid or other lipids directly to the N-terminus of A. beta as described for hepatitis B antigen vaccination (Livingston, J. Immunol. 159, 1383-1392 (1997)) or linking directly A. beta peptide to S1P. Non-liposomal adjuvants can be administered as a component of a therapeutic composition with an active agent or can be administered separately, before, concurrently with, or after administration of the therapeutic agent.

We have chosen as a preferred class of adjuvants, a liposomal formulation comprising phosphatidyl choline: phosphatidyl glycerol: Cholesterol, other adjuvant contains the most common lipaluminum salts (alum), such as aluminum hydroxide, aluminum phosphate, aluminum sulfate could also be used. Such adjuvants can be used with or without other specific immunostimulating agents such as MPL or 3-DMP, QS21, polymeric or monomeric amino acids such as polyglutamic acid or polylysine. Another micellar adjuvant is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-A1-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

The formulation preferred in certain embodiments of this invention, referred to herein as EB101, can be packaged and supplied in a vial in liquid injectable form or can be lyophilized to be reconstituted before injection. E101 is typically packaged with a label indicating the intended therapeutic application. If E101 is lyophilized, a solubilizing agent would be packaged separately, the packaging typically includes instructions for mixing before use. The choice of alternative adjuvants and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously. Preferred combinations include alum with MPL, alum with QS21, MPL with QS21, and alum, QS21 and MPL together. Also, Incomplete Freund's adjuvant can be used (Chang et al., Advanced Drug Delivery Reviews 32, 173-186 (1998)), optionally in combination with any of alum, QS21, and MPL and all combinations thereof.

Agents of the invention are often administered as pharmaceutical compositions comprising an active therapeutic agent, A. beta Peptide and S1P, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. However, some reagents suitable for administration to animals, such as Complete Freund's adjuvant are not typically included in compositions for human use.

For parenteral administration, agents of the invention, EB101 can be administered as injectable dosages of a solution or suspension of the substance in a physiologically acceptable diluent with a pharmaceutical carrier which can be a sterile liquid such as water, saline or other acceptable salts. Additionally, auxiliary substances, pH buffering substances, sucrose, glucose and the like can be present in compositions.

In the present experiments, the active ingredients, Aβ42 and S1P, are prepared as injectables, in liposomal formulations suitable for solution or lyophilized with separate liquid vehicles to be mixed prior to injection. The preparation also can be emulsified in micelles or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). The agents of this invention can be administered in the form of a depot injection or implant preparation that can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., Eur. J. Immunol. 25, 3521-24 (1995); Cevc et al., Biochem. Biophys. Acta 1368, 201-15 (1998)).

Methods of Diagnosis

The invention provides methods of detecting an immune response against A. beta peptide in a patient suffering from or susceptible to Alzheimer's disease. The methods are particularly useful for monitoring a course of treatment being administered to a patient. The methods can be used to monitor both therapeutic treatment on symptomatic patients and prophylactic treatment on asymptomatic patients.

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an agent are expected to show an increase in immune response with successive dosages, which eventually reaches the plateau. Administration of agent is generally continued while the immune response is increasing. Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent are then compared with the control value. A significant increase relative to the control value (e.g., greater than one standard deviation from the mean) signals a positive treatment outcome. A lack of significant increase or a decrease signals a negative treatment outcome. Administration of agent is generally continued while the immune response is increasing relative to the control value. As before, attainment of a plateau relative to control values in an indicator that the administration of treatment can be discontinued or reduced in dosage or frequency.

In other methods, a control value of immune response (e.g., a mean and one standard deviation) is determined from a control population of individuals who have undergone treatment with a therapeutic agent and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the levels in the patient persist below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same value) is an indication that treatment can be resumed. Alternatively, the value measured in a patient can be compared with a control value (mean plus standard deviation) determined in population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucus or cerebral spinal fluid from the patient. The sample is analyzed for indicia of an immune response to any forms of A. beta peptide, typically A. beta42. The immune response can be determined from the presence of e.g., antibodies or T-cells that specifically bind to A. beta peptide. ELISA methods of detecting antibodies specific to A. beta are described in the Examples section.

The invention further provides diagnostic kits for performing the diagnostic methods described above. Typically, such kits contain an agent that specifically binds to antibodies to A. beta or reacts with T-cells specific for A. beta. The kit can also include a label. For detection of antibodies to A. beta, the label is typically in the form of labeled anti-idiotypic antibodies. For detection of antibodies, the agent can be supplied pre-bound to a solid phase, such as to the wells of a microtiter dish. For detection of reactive T-cells, the label can be supplied as .sup.3 H-thymidine to measure a proliferative response. Kits also typically contain labeling providing directions for use of the kit. The labeling may also include a chart or other correspondence regime correlating levels of measured label with levels of antibodies to A. beta or T-cells reactive with A. beta. The term labeling refers to any written or recorded material that is attached to, or otherwise accompanies a kit at any time during its manufacture, transport, sale or use. For example, the term labeling encompasses advertising leaflets and brochures, packaging materials, instructions, DVDs, CDs, audio or videocassettes, computer discs, as well as writing imprinted directly on kits.

The following examples are provided for illustration and are not intended to limit the invention to the specific examples provided.

EXAMPLES

Example 1

Prophylactic Efficacy of A. Beta and S1P Against AD

These examples describe administration of A. beta 42 peptide and S1P in liposomes (EB101) to B6C3-Tg transgenic mice that are predisposed to develop Alzheimer's-like neuropathology. The B6C3-Tg transgenic mice carrying combined amyloid precursor protein Swedish (K670M/N671L) and presinilin 1 mutations, produce an aggressive AD pathology, evident as early as 3 months of age, that is a composite of core plaques and peculiar floccular diffuse parenchymal deposits. Alternatively, other transgenic mice carrying the Swedish mutation alone or in combination with other variants, can also be used in these tests. These alternative animals, in their heterozygote form, begin to deposit A. beta at six months of age forward. By fifteen months of age they exhibit levels of A. beta deposition equivalent to that seen in AD.

Methods

1. Source of Mice

Transgenic, B6C3-Tg(APPswe, PSEN1dE9) 85Dbo/J, mice were obtained from Jackson Labs, heterogenic female mice were randomly divided into the following groups: 10 mice to be injected with A. beta 42 and S1P in liposomes (EB101), 10 mice to be injected with liposomes alone, without A. beta and S1P (EB102), and 10 with vehicle controls.

2. Preparation of A. Beta

Two milligram aliquots of A. beta 1-42 human (TOCRIS bioscience; Tocris Cookson Ltd.; this A. beta corresponds to the human form of the predominant amyloid Beta-peptide found in the brains of patients with Alzheimer's disease) were dissolved in 0.9 ml water and made up to 1 ml by adding 0.1 ml of 10×PBS. This was vortexed and lyophilized and stored as a dry power at −20° C. until the preparation of liposomes containing A beta and S1P.

3. Preparation of Liposomes and Liposomal Injections 1,2-Dioleoyl-sn-Glycero-3-Phosphocholine (DOPC), 1-Palmitoyl-2-oleoyl-sn-glycero-3-phosphatidylglycerol, Sodium Salt (POPG), cholesterol (CH) (Northern lipids INC.) and D-erythro-Sphingosine-1-Phosphate (S1P) (AVANTI®) were used to make the liposomal preparation at a molar ratio of 0.3:0.3:0.39:0.01 respectively. One hundred milligrams of each lipid were dissolved in 1 ml of chloroform and stored at −20° C. until the preparation of the liposomes. In the case of S1P, 10 mg were dissolved in 1.5 ml 2:1 chloroform methanol and stored at −20° C. A. beta peptide, 10 mg, was dissolved in 10 ml PBS and lyophilized and stored as a dry powder until use.

The corresponding amount of each lipid, at the final molar ratio as indicated above, was thoroughly mixed and the solvent was evaporated under nitrogen. The dried lipid mixture containing total lipid 100 mg (DOPC:POPG:CH:S1P) was then hydrated in 10 ml autoclaved ultrapure water to form multilamellar vesicles (MLV). Small lamellar vesicles (SLV) or Single unilamellar vesicles (SUV) were subsequently prepared by sonicating the MLV for 2 min. at 30 seconds intervals in an ice bath until the solution became clear. To eliminate particulate material produced by sonication, a centrifugation step was done (2500 g/15 min.) and the pellet discarded. Subsequently, A. beta (total peptide 10 mg) was added to the liposomal mixture, and thoroughly vortex mixed. This preparation was then frozen under liquid nitrogen and lyophilized. The resulting freeze-dried powder was resuspended in 10 ml ultrapure autoclaved water at a final lipid concentration of 10 mg/ml and 1 mg/ml A. beta peptide and the suspension was thoroughly vortex mixed to form liposomes. This preparation is referred as EB101 and is ready for immunization. One hundred microliters of EB101 was used in each immunization to treat the group A mice.

4. Preparation of Empty Liposomes (EB102)

The same steps as for EB101 preparation were followed to prepare EB102. This liposomal mixture contains DOPC:POPG:CH, 0.3:0.3:0.4 molar ratio at the same final lipid concentrations as in EB101, but without S1P and A. beta peptide. One hundred µl EB102 was used in each injection to treat the B group of mice.

5. Immunization Regimen

Female B6C3-Tg (APPswe, PSEN1dE9) 85Dbo/J; 17 mice were inoculated intraperitoneally with 100 µl per injection of EB101 (group A), only liposomes, EB102, (group B) or vehicle (group C), over a period of 7 months (9 injections total; the first three injections were two weeks apart, and the remaining 6 injections were monthly thereafter). Mice were seven to nine months old at the first set of injections.

6. Measurement of Antibody Titers 96-well microtiter plates (Costar EIA plates) were coated with 1 µg/ml of Aβ 1-42 in well coating buffer (0.1 M sodium phosphate, pH 8.5, 0.1% sodium azide) and held overnight at RT. The wells were aspirated and sera were added to the wells at a starting dilution of 1/100 in specimen diluent (0.014 M sodium phosphate, pH 7.4, 0.15 M NaCl, 0.6% bovine serum albumin, 0.05% thimerosal). Six serial dilutions (1/400, 1/1,600, 1/6,400, 1/25,600) of the samples were made directly in the plates in two-fold steps to reach a final dilution of 1/102,400. The dilutions were incubated in the coated-plate wells for one hour at RT. The plates were then washed five times with PBS containing 0.05% Tween 20. The second antibody, a goat anti-mouse Ig conjugated to horseradish peroxidize (obtained from Boehringer Mannheim), was added to the wells (100 µl/well at a dilution of 1/4,000 in specimen diluent) and incubated for one hour at RT. Plates were again washed five times in PBS/Tween 20. To develop the chromogen, 100 µl TMB (3,3',5,5'-tetramethyl benzidine obtained from Pierce Chemicals) was added to each well and incubated for 15 minutes at RT. The reaction was stopped by the addiction of 50 µl 0.5 M H2SO4. The color intensity was then read on an ELISA plate reader (BioRad 680 ELISA Reader). Titers were defined as the reciprocal of the dilution of serum giving one half the maximum OD. Maximal OD was generally taken from an initial 1/100 dilution.

7. Spleen Cell Preparation

Splenoctyes from 14 mice were harvested from spleen tissue mechanically disrupted with forceps. Following the lysis of red blood cells (140 mM ammonium chloride in 100 mM Tris buffer. pH 7.5), splenocytes were washed twice with 1× phosphate buffer saline (PBS) pH 7.0 and centrifuged at 1600 rpm for 5 minutes, counted and 106/ml cells were resuspended in complete RPMI-1640 medium containing 10% FSC, 50 µM β-mercaptoethanol and 40 µg ml-1 gentamycin.

8. B-Cell Enriched Suspensions

B-cell-enriched suspensions were obtained using the following procedure. Briefly, macrophages from spleen cells were depleted by selective adherence to glass Petri dishes for 2 h at 37° C. Non-adherent cell suspensions were depleted of T cells by magnetic cell sorting using anti-Thy-1.2-coated magnetic beads (Dynal Biotech, France), as indicated by the manufacturer's instructions. This procedure yielded an enriched B-cell population >90% CD19+ cells with <1% CD3+ cells, and <5% CD11c+ cells as determined by flow cytometry analysis and >95% of viable cells, as determined by trypan blue exclusion.

9. B and T Cell Phenotypic Analysis by Flow Cytometry

Briefly, 1×106 red-cell-depleted splenocytes were incubated with anti-mouse CD32/CD16 antibody (control antibody) in order to block non-specific Ig trapping through Fc receptors. The following PE-conjugated anti-mouse mAbs were used for analysis: anti-CD4, anti-CD19, anti-IgM and anti-CD138 (BD PharMingen, San Diego, Calif.). Data from stained samples were acquired using a FACScan flow cytometry. A total of 15 000 events were analyzed using Lysis II software.

10. Lymphocyte Proliferation Assay

Proliferation assays were set up in triplicate, in 96-well flat bottom plates (Nunc, Naperville, Ill.). Each culture consisted of 1×105 purified B and T cells in a final volume of 200 µl. LPS (20 µg ml-1), IL-4 (100 U ml_1) plus anti-CD40 (5 µml-1) and Aβ (1 µg ml) were used. After incubation at 37° C. in 5% CO2 for 48 h, the proliferative response was monitored by MTT assay, based on the cleavage of the yellow tetrazolium salt MTT to purple formazan crystal by metabolic active cells. The formazan is then solubilized, and the concentration determined by optical density at 570 nm. In brief, cells were seeded into 96-well tissue culture plates at a density of between 5000 cells per well. After stimulation, 10 µL of MTT solution were added to each well. Plates were mixed by briefly shaking on an orbital shaker. Plates were incubated at 37° C. for 4 hours.

Medium was removed and 200 µL DMSO was added into each well to dissolve the formazan by pipetting up and down several times. Absorbance was measured on an ELISA plate reader with at a wavelength of 570 nm. The results obtained from triplicate assays were express as stimulation indexes (ratio between mean OD from stimulated cultures and mean OD from unstimulated cultures). Values are representative of at least three independent experiments.

11. Neuropathology.

While anesthetized, the animals were perfused transcardially first with NaCl solution and then with 4% paraformaldehyde, and their brains were excised and immersed in the same fixative for 48 hours, then immersed in phosphate buffer 0.1M (12 h) and cryoprotected with 30% sucrose in PB, embedded in OCT compound (Tissue Tek, Torrance, Calif.), and frozen with liquid nitrogen cooled isopentane. Parallel series of transverse sections (18/20 µm thick) were cut on cryostat and mounted on Superfrost Plus (Mnzel Glasser, Madison, Wis.) slides.

12. A. Beta Peptide Quantification, Neurofibrillary Tangles and Apoptosis Analysis The following antibodies were used: Anti-amyloid β (Aβ) x-42 monoclonal antibody (Millipore) which recognizes amyloid βx-42 polypeptide Mr. 4.5 kDa.; Anti-Alzheimer's Disease Tau monoclonal antibody (Sigma), which recognize tau phosphorylated (residues 151/421). Anti-Neurofibrillary tangles rabbit polyclonal antibody (Millipore); Anti-synaptophysin monoclonal antibody (Sigma); Anti-glial fibrillary acidic protein monoclonal antibody (Sigma); Anti-Human CD45RA (Dako) monoclonal antibody and Anti-Human CD3 (Dako) rabbit polyclonal antibody, which recognizes B-cells and T-cells, respectively. The NeuroTACS™ II In Situ Apoptosis Detection Kit (Trevigen) was used for the detection of apoptosis in tissue sections.

13. Histologic and Immunohistochemical Analysis

For immunohistochemical analyses, parallel sections were pretreated with $H_2O_2$, in phosphate-buffered saline (PBS) at 37° C. for 15 minutes to eliminate endogenous peroxidase, rinsed twice in 0.05M Trizma buffered saline containing 0.1% Tween-20 at pH 7.4 (TBS-T), 10 minutes each, pretreated with blocking Avidin/Biotin kit and then incubated overnight with the primary antibodies. The procedure provided by the mouse-on-mouse peroxidase immunodetection system (M.O.M. Kit; Vector) was used to eliminate any nonspecific binding of anti-mouse secondary antibodies with the endogenous mouse immunoglobulins in the tissue, according to manufacturer's instructions. The sections were successively rinsed in TBS-T, incubated in goat IgG antirabbit (Dako) or goat IgG antimouse (Dako), depending on the primary antibody, for 1 hour, rinsed in TBS-T and then incubated for 30 minutes in ABC kit system (Vectastain; Vector). Peroxidase reaction was performed with 3,3-diaminobenzidine as chromogen and hydrogen peroxide as oxidant. In several adjacent sections, negative controls performed by omitting the primary, secondary or tertiary antibodies showed no immunostaining. Sections were then dehydrated in graded ethanol and covered with a rapid embedding agent (Eukitt; Fluka). Images were visualized using a microscope (Olympus BX50) and were digitized via a digital camera (DP-10; Olympus). The photographs were then adjusted for brightness and contrast with Corel Photo-Paint (Corel, Ottawa, Canada) and plates were composed with Corel Draw.

14. Confocal Analysis

Individual Immunofluorescent sections were photographed with a Spectral Confocal Laser Scanning Microscope (Leica TCS-SP2). Plaques were imaged at the level of their largest cross-section, and their size determined by using the Leica processing software. This methodological approach was used to compare NT-AP (FIG. 10), NT-GFAP (FIG. 11) and NT-Bcells (FIG. 12) immunostainings. Two brain regions (hippocampus and enthorhinal cortex) per animal were analyzed. Imaging of the NT immunostaining was revealed with a fluorescein isothiocyanate filter (excitation at 488 nm), and Aβ/GFAP/Bcells staining were imaged with a Texas Red filter (excitation at 568 nm).

15. AD Markers Quantification

In immunized animals, the burden of β-amyloid plaques was determined in 7 randomly selected microscopic transverse sections per animal, defined by the stereotaxic Bregma coordinates (−0.94; −1.34; −1.70; −2.30; −2.70; −3.64; −4.60 mm). A total of 7 selected sections per animal were evaluated. The same procedure was undertaken to the neurofibrillary tangles, activated microglia, apoptotic cells, B and T cells. The quantitative assessment of burden positivity was performed by two independent observers. In cases in which significant discrepancies were obvious between the 2 observers, the evaluation was repeated by a third observer.

Quantitative analysis of amyloid burden area was also performed in the hippocampal and cortical regions of APP/PS1 Tg mice in the three treatment groups. We used an area/pixels analysis software (Pixcavator), to quantify the number of pixels inside its outer boundary of each Aβ plaque for one brain section. Therefore, Pixc imaging was used to analyze the area occupied by A. beta peptide (Aβ load) relative to the background and expressed in the percentage units. The area of A. beta peptide plaques of the brain of three treatment groups were analyzed and represented in graphics.

16. Statistical Analysis

All statistical parameters used in the present study were calculated using Microsoft Office Excel. Statistically significant differences were obtained using an analysis of variance following Tukey's or Bonferroni's multiple comparison post-test, a $p<0.05$ value was considered significantly different.

B. Results

1. A. Beta Peptide Antibody Detection.

A. beta peptide in the serum of mice was quantified by ELISA as described in methods. The background OD value for ELISA was less than 0.08 and no IgG antibody was detected in the control group. Antibodies to A. beta peptide were detected in 5 out of 6 animals vaccinated with EB101 (FIG. 1). One animal remained unresponsive. A. beta peptide led to a high increase of IgG antibody production as shown in FIG. 2.

2. Splenocyte Proliferation Response.

Figure 3:
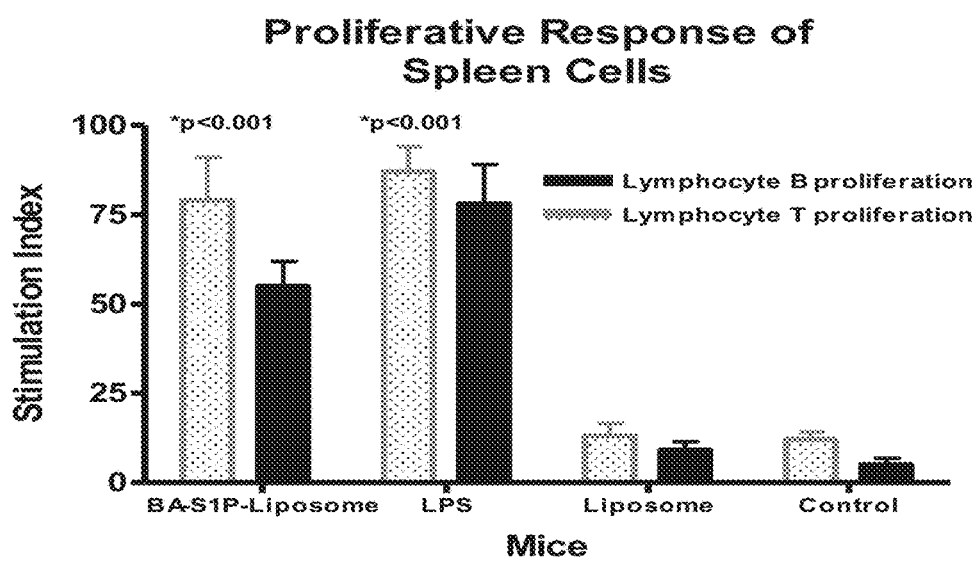
FIG. 3. shows proliferative response of spleen cells from EB101-immunized mice and controls. The results obtained from triplicate assays were express as stimulation indexes (ratio between mean OD from stimulated cultures and mean from unstimulated cultures).

At the end of the immunization period, mice in each group were killed to conduct B and T cell immunological response. The results seen in FIG. 3 show that EB101 and EB102 induced B and T lymphocyte proliferation. EB101 vaccine resulted in an enhanced proliferation response compared with mice treated with EB102 or with vehicle in five out six immunized mice ($P<0.01$).

3. A. Beta Peptide Immunochemistry and Quantitative Analysis in the Hippocampus and Cortical Regions.

Figure 4:
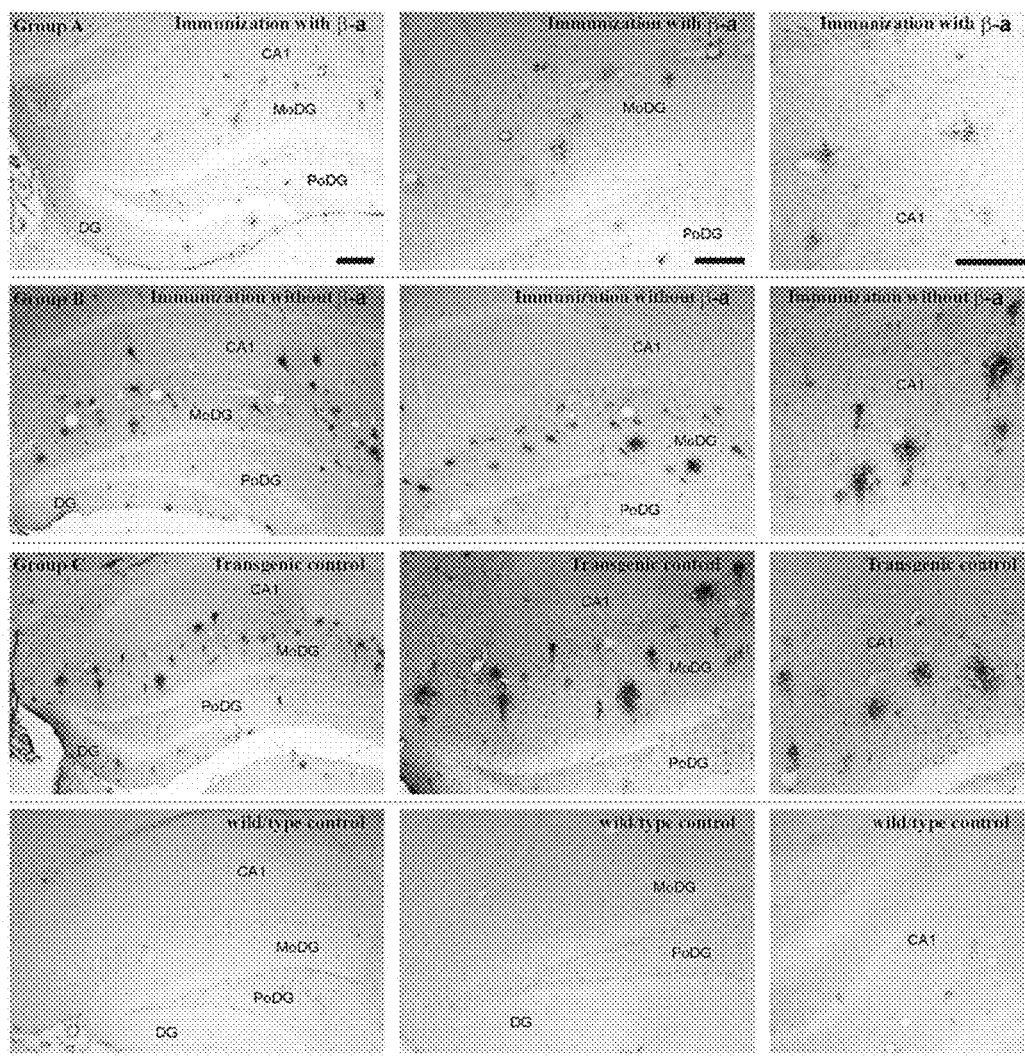
FIG. 4. shows that EB101-immunization reduces amyloid deposits in the brains of Tg(APP/PSEN)-AD mice. Comparative image of hippocampus showing significant reduction in Aβ load after administration of Aβ-immunization compared with that of mice without-Aβ injection and control (group B and C). Note the absence of immunoreactivity in the wild/type sections. Scale bars: 100 μm.
Figure 5:
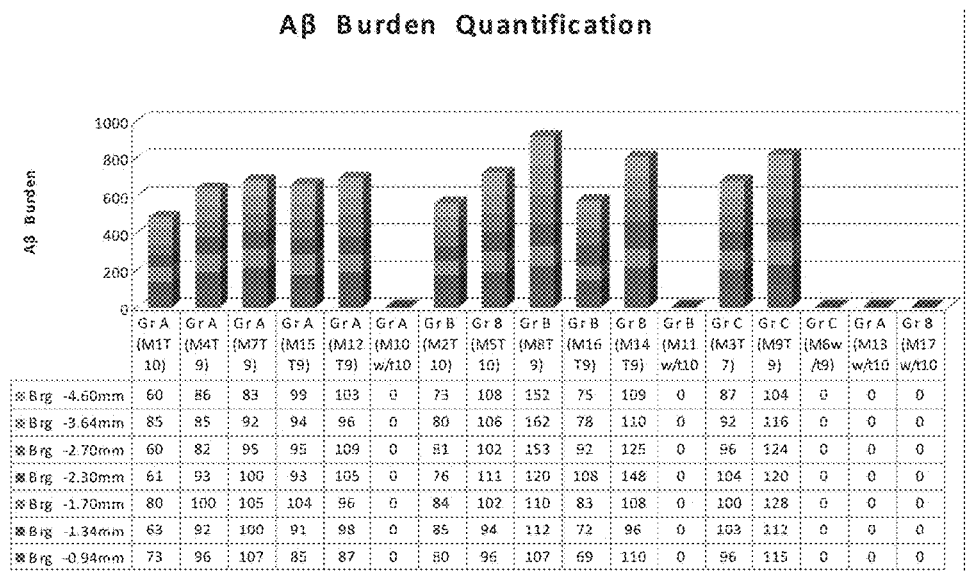
FIG. 5. shows that quantitative analysis of amyloid burden in the hippocampal and cortical regions of APP/PS1 Tg and control mice. Seven brain sections were immunolabeled for Aβ, being analyzed by optical microscopy as described in the Examples. Representation Aβ burden for each brain section, showing that Aβ burden is decreased in these brain regions of APP/PS1 Tg mice immunized with the EB101 vaccine complex (group A).

The experiments carried out in 5 transgenic mice and 2 wild type mice show the effects of the immunization with EB101 on A. beta peptide deposition before the appearance and during the early onset of the AD-like neuropathology. Comparative studies were carried out in the three groups, group A, immunized with EB101, and with the two other groups treated with only the liposome complex, EB102, (7 mice) or with vehicle (3 mice). FIG. 4 shows the result in these three groups at the end of 9 immunizations over a period of 7 months. EB101 considerably reduces A. beta peptide plaques as shown by the immuhistochemical analysis. Quantitative immunohistochemistry of A. beta peptide load were performed to determine the extent of β-amyloid plaque burden. FIG. 5 shows a reduction by EB101 on A. beta burden in the hippocampal and cortical regions compared to the other two non-immunized groups.

Figure 16:
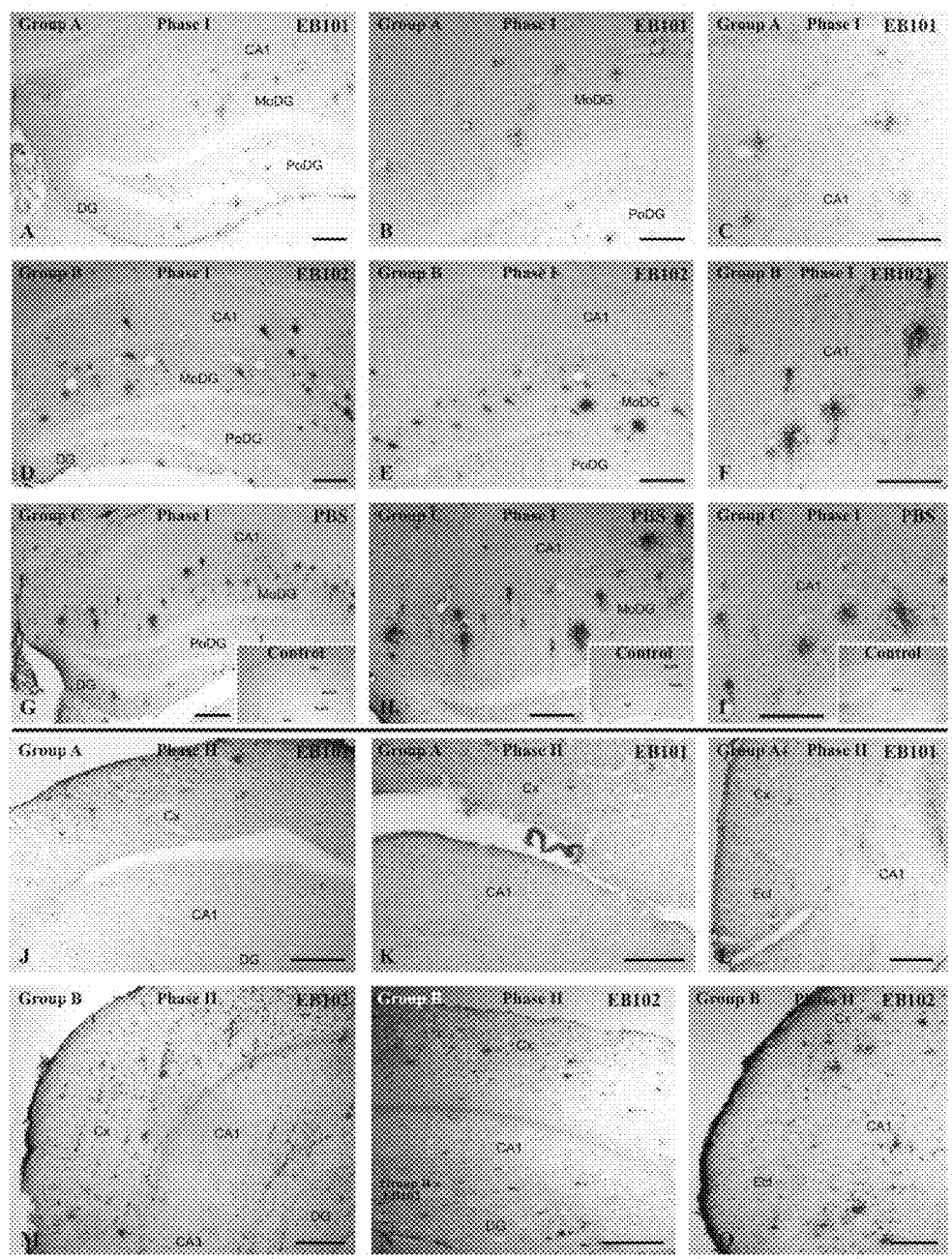
FIG. 16 shows photomicrographs of brain sections demonstrating the results of experiments showing that an EB101 vaccine reduced amyloid deposits in the brain of PS1/APP transgenic mice.

See also FIG. 16, which shows results of experiments showing that an EB101 vaccine reduced amyloid deposits in the brain of PS1/APP transgenic mice. Comparative Aβ immunoreactivity of APS1/APP transgenic mice is shown in photomicrographs of hippocampus and cortical brain regions after the prophylactic (images A-I; Phase I, Groups A-C) and therapeutic treatment (J-O; phase II, group A and B)) experimental periods. Photomicrographs A-I show transverse brain sections of 15-month-old mice after prophylactic treatment with EB101, indicating almost complete prevention of Aβ load after EB101 vaccine immunization (A-C) compared with EB102 immunized treated mice (D-F), PBS (G-I) and control groups (squared areas in figures G-I). Photomicrographs A-C show transverse sections of the dentate gyms (A,B) and hippocampal subregion CA1 (C), indicating scarce and sparse Aβ plaques with week immunoreactivity in the dentate gyms, contrasting sharply with the numerous Aβ immunoreactive plaques in the corresponding brain mice sections of Phase I Groups B (D-F; EB102) and C (G-I; PBS). Note the abundant density of Aβ immunoreactive plaques (F,I), as well as their extensive size and stronger immunolabeling as compared with Group A brain section (C). Photomicrographs J-O show transverse brain sections of 21-month-old mice of the therapeutic treatment period, indicating almost complete reduction of Aβ load after EB101 vaccine immunization (J-L) compared with EB102 immunized mice (M-O), PBS and control groups. Photomicrographs J-L show transverse sections of the restrosplenial cortex/hippocampal subregion CA1 (J, K) and ectorhinal cortex (L), showing a few small sparse Aβ plaques with almost complete absence of immunoreactivity, being confined in the external cortical layers, which contrasts markedly with the elevated density of Aβ immunoreactive plaques in the corresponding brain mice sections of Group B (M-O; EB102). Note the abundant density of Aβ immunoreactive plaques (M-O), as well as their extensive size and stronger immunolabeling when compared with Group A brain section (J-L). Scale bar: 100 µm.

4. Characterization and Quantification of A. Beta Peptide-Plaques in B6C3-Tg Mice.

In the present study we identified four different types of A. beta peptide plaques based on their morphology. Type 1 plaques were devoid of a central dense core displaying an irregular shape; Plaques type 2a exhibited a central core surrounded by a corona of fibrillar material; Plaque 2b was characterized by fibrillar material radiating from the central dense core; Plaques type 2c, also called "burned-out" plaques by analogy with human classifications, were strongly β-amyloid-positive without any surrounding weakly reticular material. Compact deposits type 2c displaying a cross-section with smaller granules and were not taken into account.

Figure 6:
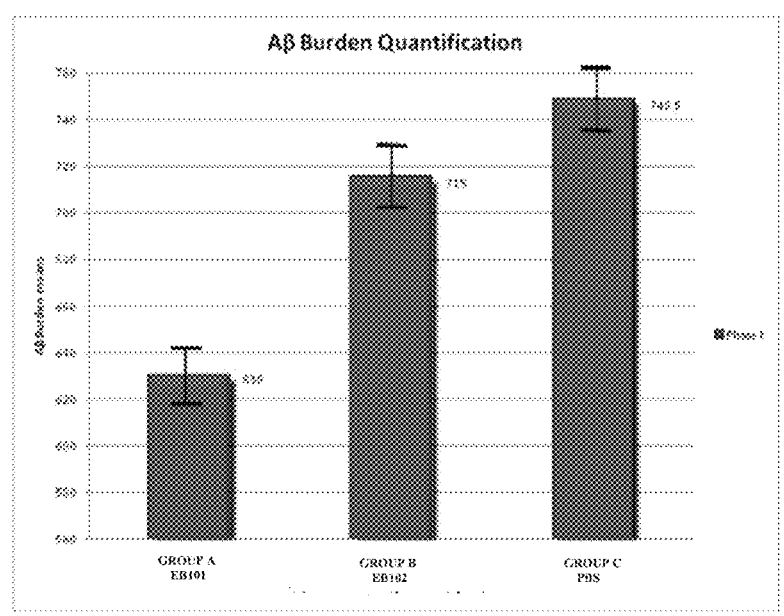
FIG. 6. shows that quantitative analysis of amyloid burden means in the hippocampal and cortical regions of APP/PS1 Tg mice in the three treatment groups. The Aβ burden mean is decreased in group A (EB101 vaccine treatment) when compared with B and C.
Figure 7:
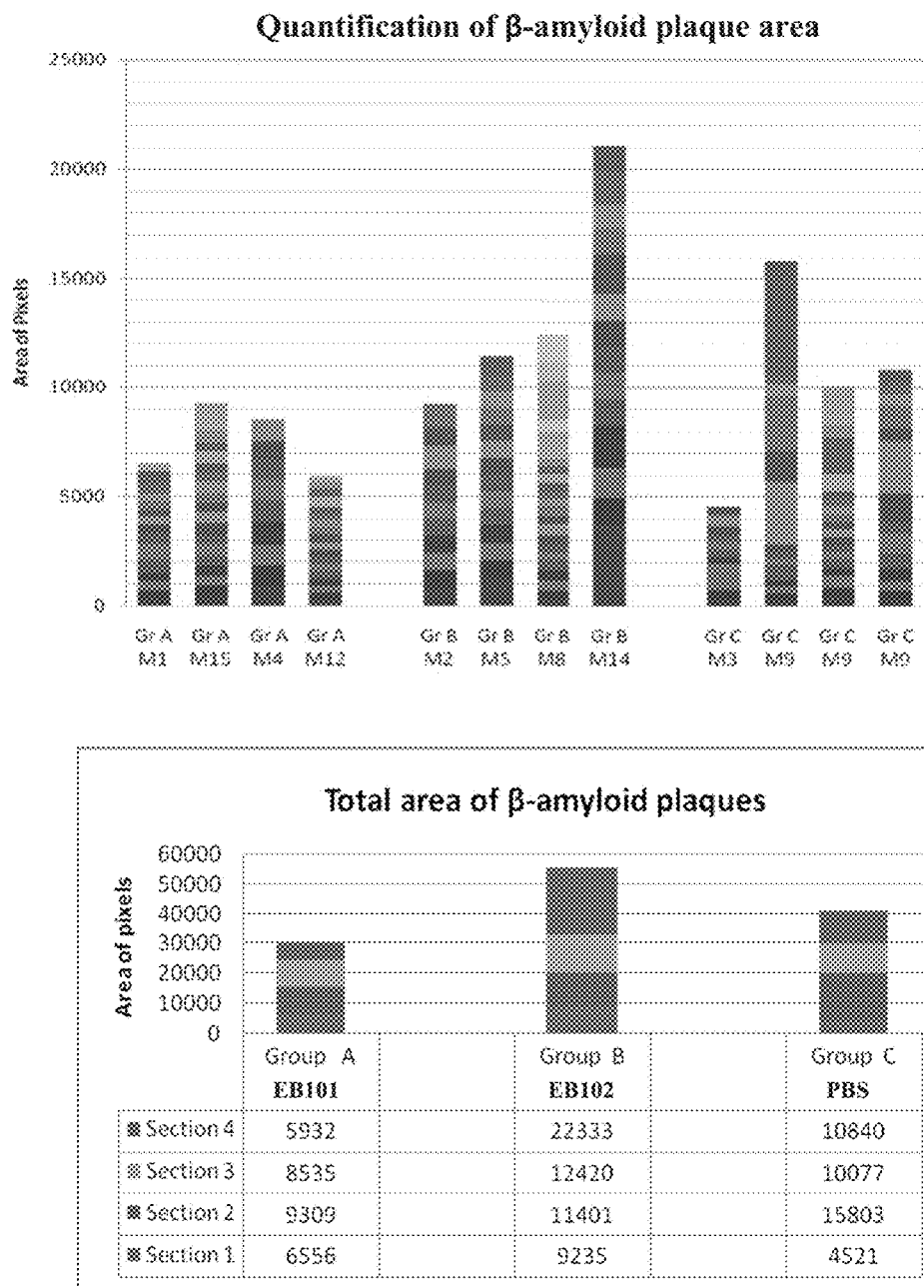
FIG. 7. shows that quantitative analysis of amyloid burden area in the hippocampal and cortical regions of APP/PS1 Tg in the three treatment groups. The representation of the number of pixels inside its outer boundary of each Aβ plaque for one brain section, showing that Aβ plaques of group A mice brains are smaller in size than those of the other two treatment groups (B and C).

The results obtained in non-treated B6C3-Tg (group C) after the prophylactic immunization period showed many of the pathological features of AD, including extensive deposition of extracellular A. beta peptide plaques, astrocytosis, and neurotic dystrophy. A histological analysis of this B6C3-Tg mice revealed that β-amyloid plaques were mainly present in the hippocampus, specially loaded into dentate gyrus (granular layer), followed by neocortical regions such retrosplenial areas, ectorhinal and piriform cortex layers (FIG. 5). In EB101-treated transgenic mice the area of A. beta peptide deposits (Aβ burden) in both the hippocampus and cerebral cortex after seven months of active immunization is significantly lower than in group B, treated with EB102 (FIGS. 5 and 6) except in one mouse (M16TB9). Group C mice showed variable density of Aβ burden but in all cases much higher than in group A. All wild-type mice showed no A. beta peptide deposits in any brain region (FIG. 7).

5. Neurofibrillary Tangles

Figure 8:
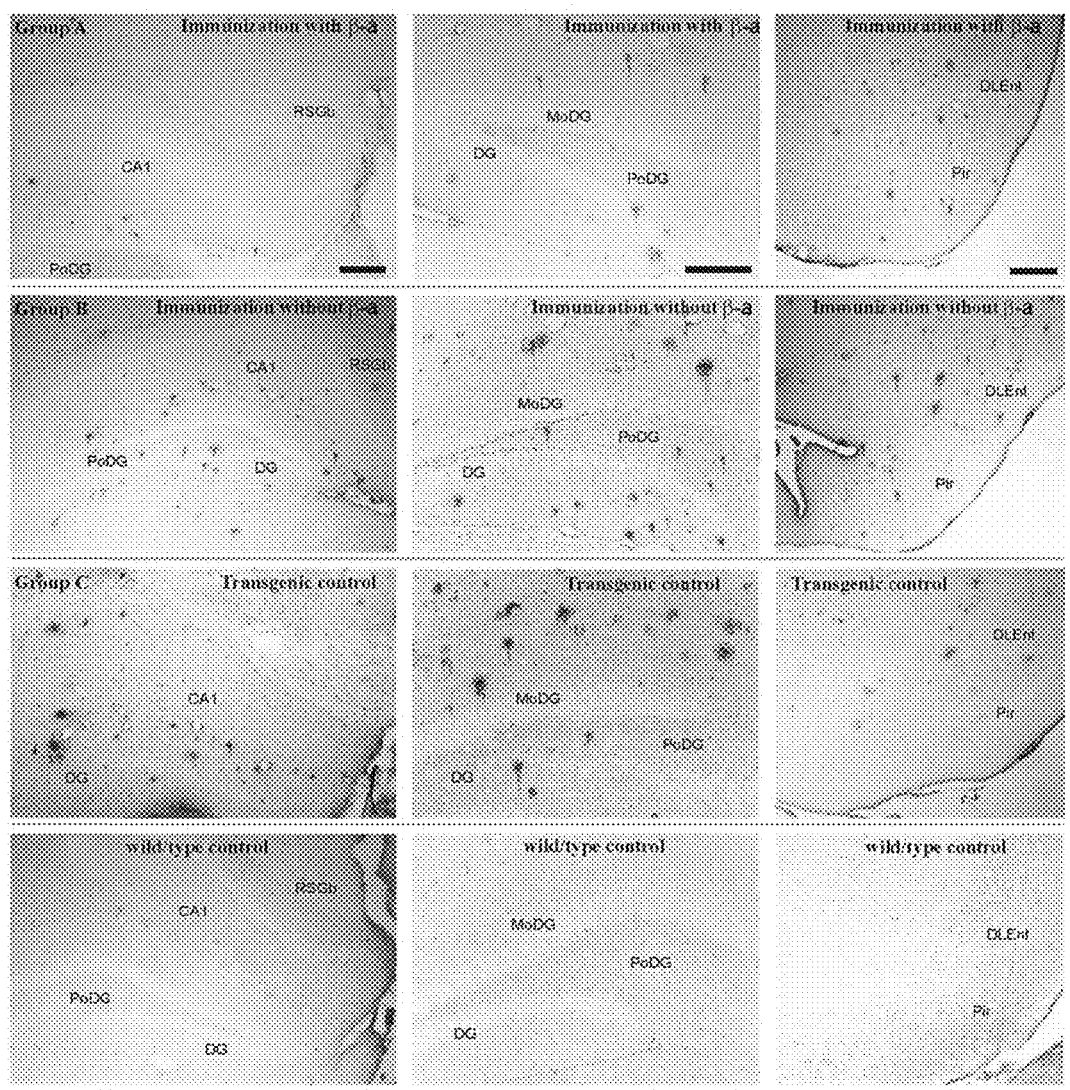
FIG. 8. shows that EB101-immunization reduces neurofibrillary tangles in the brains of Tg(APP/PSEN)-AD mice. Comparative image of hippocampus showing significant reduction in neurofibrillary tangles after administration of EB101 compared with that of mice without-Aβ injection and control (group B and C). Note the absence of immunoreactivity in the wild/type sections. Scale bars: 100 μm.

Antibodies to neurofibrillary tangles stained positive for neuritic plaques in groups A, B and C, although the density of these neuritic plaques is substantially reduced by EB101 immunization, group A, as shown in FIG. 8. The neuritic plaques are composed mainly by aggregation of hyperphosphorylated tau protein along the neuronal helical filaments; they show a plaque-like immunoreactive core with an apical variable dendrite extension, often having a flame-shape appearance (FIG. 8). In the main affected areas of the brain, (hippocampus regions, retrosplenial areas, ectorhinal and piriform cortex), the density of these neurofibrillary tangles per section were much more abundant in non EB101-treated mice (group B and C), where the distribution of these plaques was also wider. The wild-type mice showed no plaques in any brain region.

Figure 13:
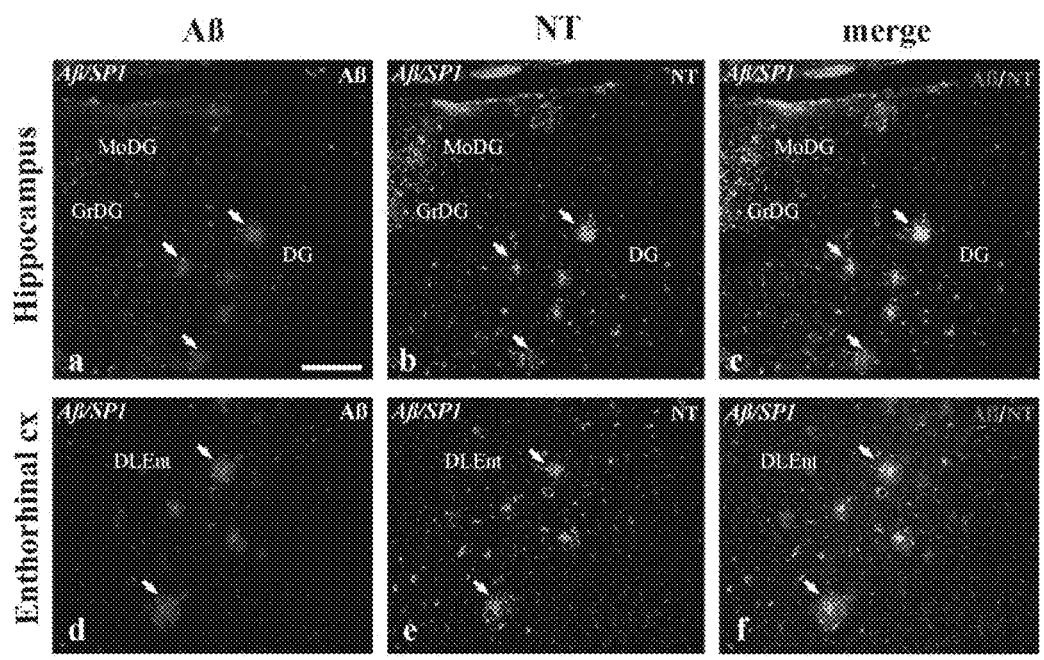
FIG. 13. shows double immunofluorescence to Aβ and neurofibrillary tangles (NT) in hippocampus and enthorhinal regions of APP/PS1 Tg mice immunized with EB101 from 7 months of age. Both brain sections were immunolabeled for Aβ (red) and NT (green), being analyzed by confocal microscopy as described in Material and Methods. (a-c) Two separate images of the hippocampus and their merge image to show co-localization of some sparse plaques (white arrows) immunofluorescence to both Aβ/NT antibodies at the molecular layer of the dentate gyms. (d-f) Co-localization of both antibodies was also observed (white arrows) at the level of the enthorhinal cortex. Scale bar: 100 μm.
Figure 14:
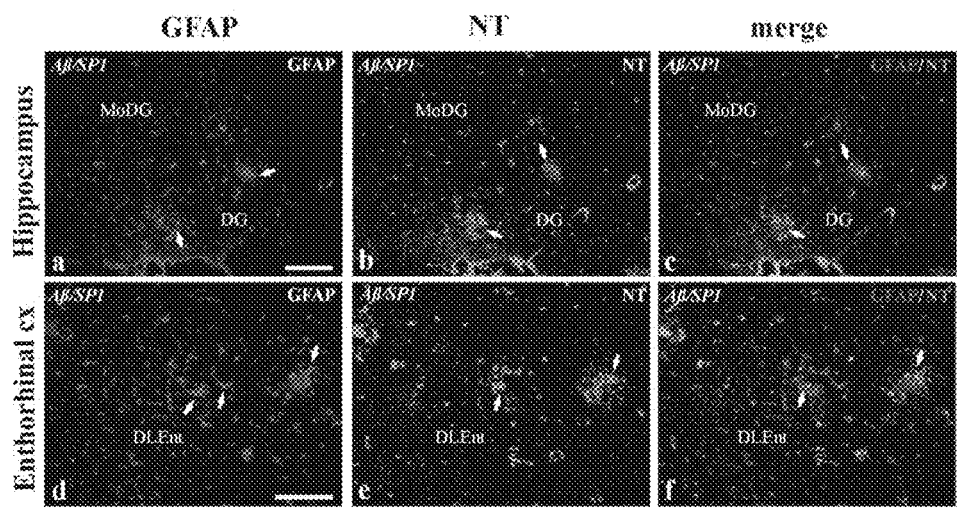
FIG. 14. shows double immunofluorescence to Glial fibrillary acidic protein and Neurofibrillary tangles in hippocampus and enthorhinal regions of APP/PS1 Tg mice immunized with EB101 from 7 months of age. Both brain sections were immunolabeled for GFAP (red) and NT (green), being analyzed by confocal microscopy as described in Material and Methods. (a-c) Two separate images of the hippocampus and their merge image to show glial cells (white arrows in a) surrounding the neurofibrillary tangles (white arrows in b) observed in this area of the dentate gyrus. Note that no co-localization was observed. (d-f) The same pattern was observed at the level of the enthorhinal cortex (white arrows from d to f). Scale bar: 100 μm.
Figure 15:
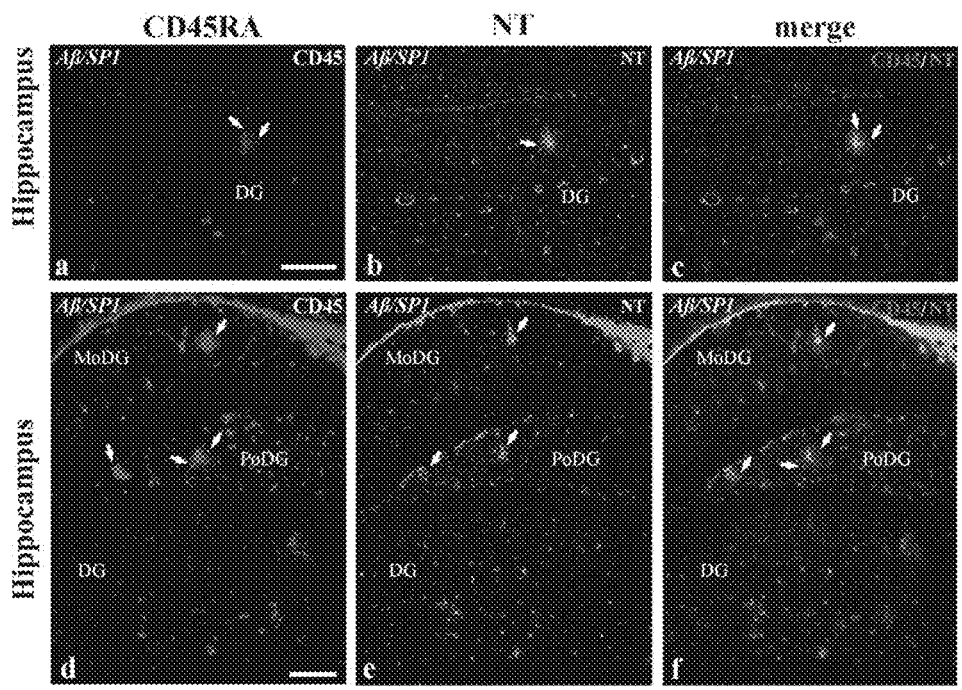
FIG. 15. shows double immunofluorescence to CD45RA (B-cells) and neurofibrillary tangles in two hippocampal regions of APP/PS1 Tg mice immunized with EB101 from 7 months of age. These brain sections were immunolabeled for CD45 (red) and NT (green), being analyzed by confocal microscopy as described in Material and Methods. (a-c) Two separate images of the dentate gyrus and their merge image to show B-cells (white arrows in a) surrounding the neurofibrillary tangle (white arrow in b). Note some co-distribution of B-cells and neurofibrillary tangles in this area (white arrow in c). (d-f) The same pattern was observed at the polymorph and molecular layers of the dentate gyrus (white arrows from d to f). For abbreviations, see list. Scale bar: 100 μm.

Double immunofluorescence to Aβ and Neurofibrillary tangles in hippocampus and enthorhinal regions of B6C3-Tg mice in this study immunized with EB101 show co-localization of some sparse plaques with immunofluorescence to both A. beta peptide and neurofibrillary tangles as detected by the corresponding antibodies in the molecular layer of the dentate gyrus and in the enthorhinal cortex (FIG. 13). Double immunofluorescence to glial fibrillary acidic protein and neurofibrillary tangles in hippocampus and enthorhinal regions show some glial cells surrounding the neurofibrillary tangles in the dentate gyrus and at the enthorhinal cortex, although no co-localization was observed (FIG. 14). Double immunofluorescence to CD45RA (B-cells) and neurofibrillary tangles in two hippocampal regions of mice immunized with EB101 were also analyzed by confocal microscopy, showing B-cells surrounding the neurofibrillary tangle where some co-distribution was observed in the polymorph and molecular layers of the dentate gyrus (FIG. 15).

Figure 17:
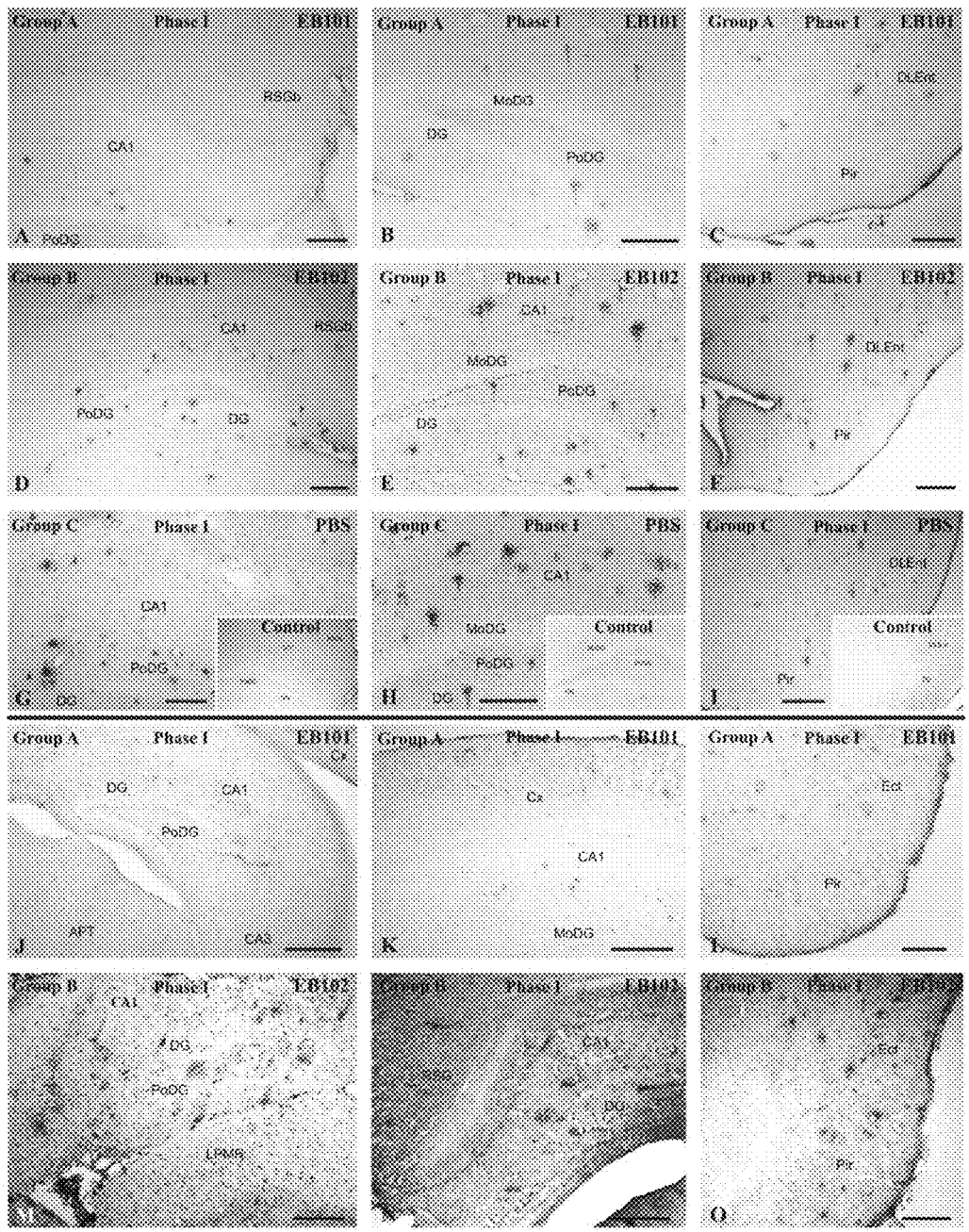
FIG. 17 shows that the EB101 vaccine reduces neurofibrillary tangles in the brains of PS1/APP transgenic mice. Comparative photomicrographs of hippocampus and cortical brain regions are from preventive (A-I; phase I) and therapeutic treatment (J-O; phase II) experimental periods.

Results of additional experimental work are shown in FIG. 17, which demonstrates that the EB101 vaccine reduces neurofibrillary tangles in the brains of PS1/APP transgenic mice. Comparative photomicrographs of hippocampus and cortical brain regions at preventive (A-I; phase I) and therapeutic treatment (J-O; phase II) experimental periods showing NT immunoreactivity. Photomicrographs A-I show transverse brain sections of 15-months-old mice during the preventive prophylactic period after treatment with EB101, which show an almost complete prevention of the appearance of neurofibrillary tangles after EB101 vaccine immunization (A-C), compared with EB102-immunized mice (D-F), PBS (G-I) and control groups (squared areas in figures G-I). Photomicrographs A-C show transverse sections of the hippocampal (A,B) and cortical regions (A,C), showing a few sparse immunoreactive tangles with a reduced immunoreactivity, in sharp contrast to the numerous neurofibrillary immunoreactive tangles in the corresponding brain mice sections of groups B (D-F; EB102) and C (G-I; PBS). Note the abundant density of neurofibrillary immunoreactive tangles in these two groups (D,I), although the hippocampal regions of group B (D,E) shows slightly less density of immunoreactive NT compared with those of group C (G,H). J-O. Transverse brain sections of 21-months-old mice during the experimental treatment period, showing almost complete reduction of NT after EB101 vaccine immunization (J-L) in the mice treated with EB101, compared with EB102 immunized treated mice (M-O), PBS and control groups. J-L. Transverse sections of the dentate gyrus (J) restrosplenial cortex/hippocampal subregion CA1 (K) and ectorhinal cortex (L) of EB101 treated mice show a few small sparse neurofibrillary immunoreactive tangles with a reduced immunoreactivity, in marked contrast to the numerous strongly immunoreactive neurofibrillary tangles observed in the correspondent brain mice sections of group B (M-O; EB102). Scale bar: 100 µm.

Figure 20:
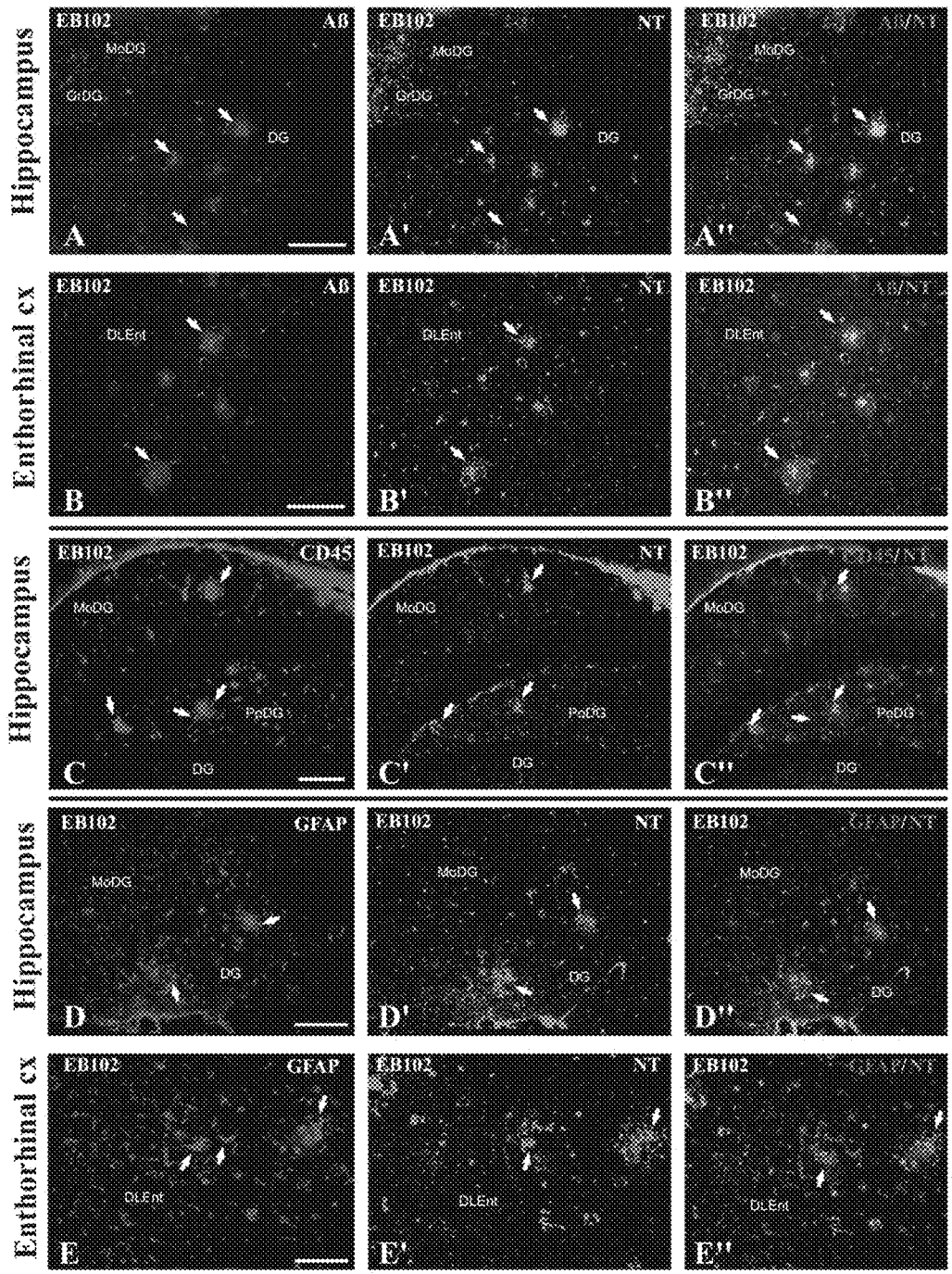
FIG. 20 shows the association of neurofibrillary tangles with activated microglia, AB deposits and B-cells in PS1/APP mouse brain.

See also FIG. 20, which shows the association of neurofibrillary tangles with activated microglia, AB deposits and B-cells in PS1/APP mouse brain. FIG. 20 shows transverse sections of double transgenic APP/PS1 mice showing double immunofluorescence to Neurofibrillary tangles, Aβ and glial fibrillary acidic protein GFAP in hippocampus and entorhinal brain regions at 7 months of age. A-B; Photomicrographs of transverse brain sections at hippocampus (A-A") and entorhinal cortex (B-B") showing immunofluorescence to Aβ (red), NT (green) and merged channels (yellow). Note some double labelled sparse plaques (white arrows) immunofluorescence to both Aβ/NT antibodies at the molecular layer of the dentate gyms (A-A") and at the entorhinal cortex level (B-B"). C; Photomicrographs of transverse brain sections at hippocampus (C-C") showing immunofluorescence to CD45-B cells (red), NT (green) and merged channels (yellow). Note some co-distribution of B-cells and neurofibrillary tangles (yellow) in this region (white arrow in C") where neurofibrillary tangle (white arrow in C') are surrounded by some B-cells (white arrows in C). D-E; Photomicrographs of transverse brain sections at hippocampus (D-D") and entorhinal cortex (E-E") showing immunofluorescence to GFAP (red), NT (green) and merged channels (yellow). Note glial cells (white arrows in a) surrounding the neurofibrillary tangles (white arrows in b) at the dentate gyms and at the level of the entorhinal cortex (white arrows from d to f), although no co-localization was observed. Scale bar: 100 µm.

6. Astrocytosis and Reactive Glial Response

Figure 9:
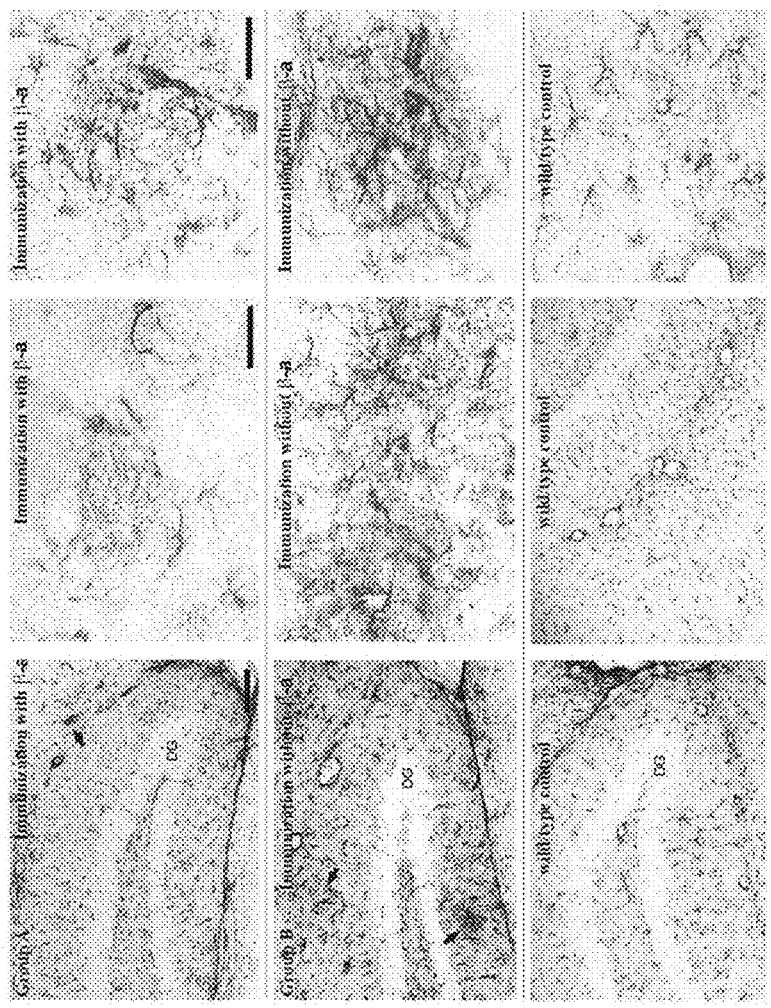
FIG. 9. shows comparative images of hippocampus showing that EB101-immunization reduces dramatically astrocytosis in the brains of Tg(APP/PSEN)-AD mice.

In order to determine the effects of the prophylactic immunization with EB101 in these transgenic mice brains, we have also analyzed the expression of the astrocyte marker, glial fibrillary acidic protein (GFAP). Activated or reactive glia were clearly observed surrounding neuronal A. beta plaques and neurofibrillary tangles, FIG. 13, shows a conspicuous morphology in the main brain regions related to AD hallmarks (FIG. 9). In all cases studied, we have found that the glial activation markers of treated mice with EB101 of group A show a substantial reduction in both density and immunoreactivity in relation to the group B and C, FIG. 9. Brains of mice treated with EB101 also show fewer A. beta-plaque-associated gliosis (aggregates of astrocytes replacing nearby dead neurons) compared with non-A. beta peptide-treated mice, groups B and C, as identified by GFAP-stained immunochemistry. The wild-type mice group showed a typical distribution of astrocytes throughout the brain regions, with no astrocytosis observed (FIG. 9).

Figure 18:
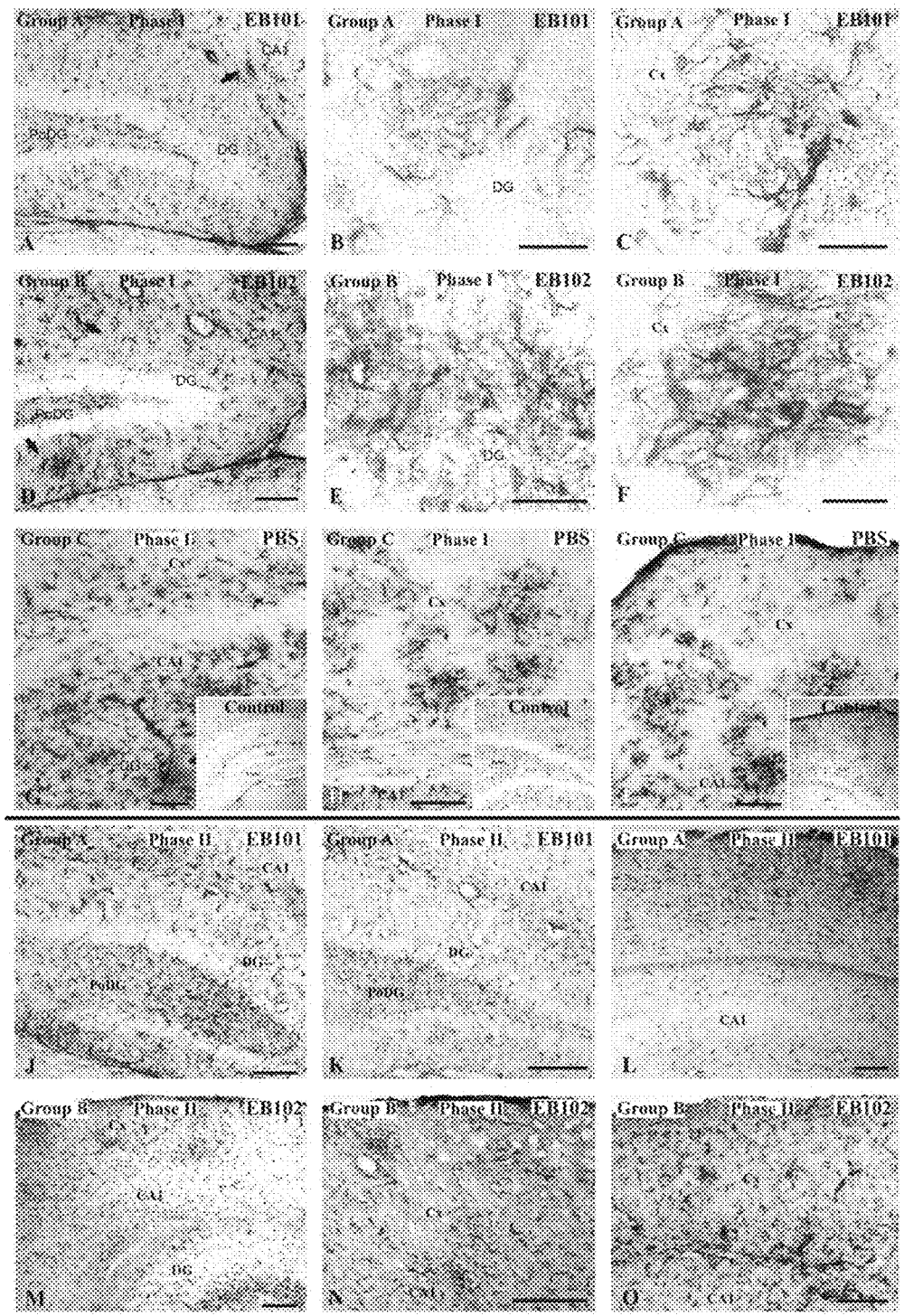
FIG. 18 shows that the EB101 vaccine dramatically reduces astrocytosis in the brains of PS1/APP transgenic mice. Comparative photomicrographs of hippocampus and cortical brain regions from preventive (A-I; phase I) and therapeutic (J-O; phase II) experimental periods showing GFAP immunoreactivity.

FIG. 18 also shows that the EB101 vaccine dramatically reduces astrocytosis in the brains of PS1/APP transgenic mice. Comparative photomicrographs of hippocampus and cortical brain regions from preventive (A-I; phase I) and therapeutic (J-O; phase II) experimental periods showing GFAP immunoreactivity. Photomicrographs A-I show transverse brain sections of 15-month-old mice from the preventive period treated with EB101, demonstrating that an almost complete prevention of astrocytosis was observed after EB101 vaccine immunization (A-C), compared with EB102 immunized treated mice (D-F), PBS (G-I) and control groups (squared areas in figures G-I). Photomicrographs A-C show transverse panoramic (A) and detailed (B) sections of the dentate gyrus and retrosplenial cortex in detail (C) to show scarce dystrophic astrocytes, which contrasts with densely dystrophic reactive astrocytes observed in the correspondent brain mice sections of groups B (D-F; EB102) and C (G-I; PBS). Note the abundant density of dystrophic reactive astrocyte clusters in groups B and C, showing a typical pathological inflammatory pathological pattern. Photomicrographs J-O show transverse brain sections of 21-month-old mice, showing almost complete reduction of astrocytosis after EB101 vaccine immunization (J-L) compared with EB102 treated mice (M-O), PBS and control groups. Photomicrographs J-L show transverse sections of the dentate gyrus (J,K) and retrosplenial cortex/hippocampal subregion CA1 (L) showing areas devoid with none (J,K) or with very few visible reactive astrocyte clusters (L), which are mainly located at the external cortical layers. This organized astrocyte pattern contrasts was with the numerous immunoreactive GFAP clusters observed in the correspondent brain mice sections of the group B (M-O; EB102). Scale bar: 100 µm.

7. Immune System

Sections of mice brains were also stained with antibodies that recognize T-cell (CD3) or B-cell (CD45RA) surface markers. B-cell labeling was abundant in EB101-treated mice (group A), especially at the hippocampal regions (FIG.

Figure 10:
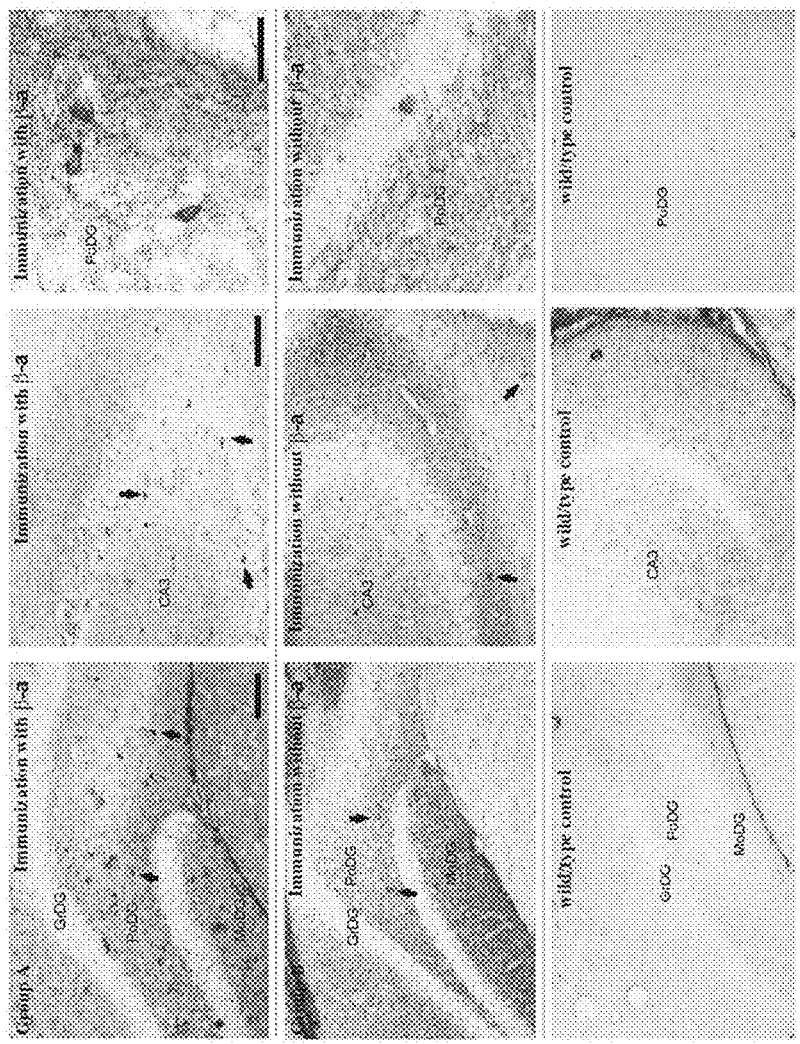
FIG. 10. shows that EB101-immunization increases B-cells in the brains of Tg(APP/PSEN)-AD mice. Comparative image of hippocampus showing abundant B-cells in EB101-treated mice after administration compared with that of mice without-Aβ injection (group B). Note the normal levels of B-cells in the wild/type sections. Scale bars: 100 μm.

10), although this surface marker was substantially lower in the mice brains of group B (non-A. beta peptide treated). Very few or no such immune cells were observed in any of the wild-type mice (FIG. 10).

Figure 11:
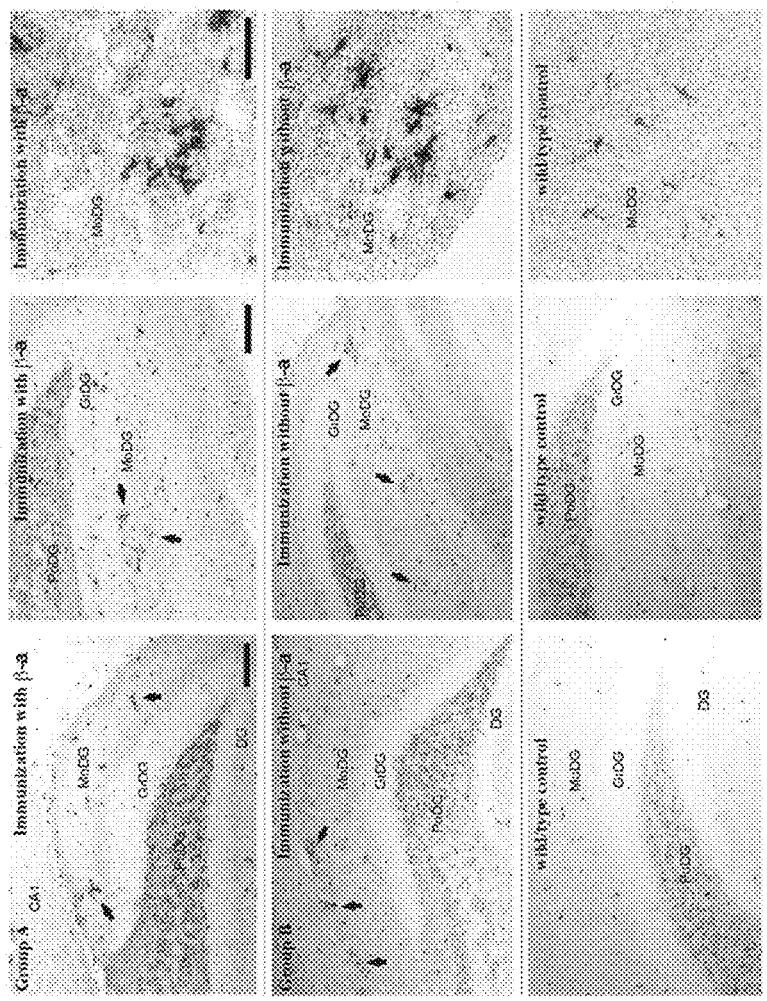
FIG. 11. shows that EB101-immunization reduces T-cells in the brains of Tg(APP/PSEN)-AD mice. Comparative image of hippocampus showing significant reduction in T-cell aggregations in EB101-treated mice compared with that of mice treated with EB102(group B) or vehicle (group C). Note the normal levels of T-cells in the wild/type sections. Scale bars: 100 μm.

Immunoreactive T-cells (FIG. 11) were identified forming conspicuous aggregates in the hippocampal and cortical regions in the group A and B, although these "immune T-cell aggregates" were slightly lower in the mice brains of group A (EB101-treated). No such immune cell aggregates were observed in the wild-type mouse (FIG. 11).

Figure 19:
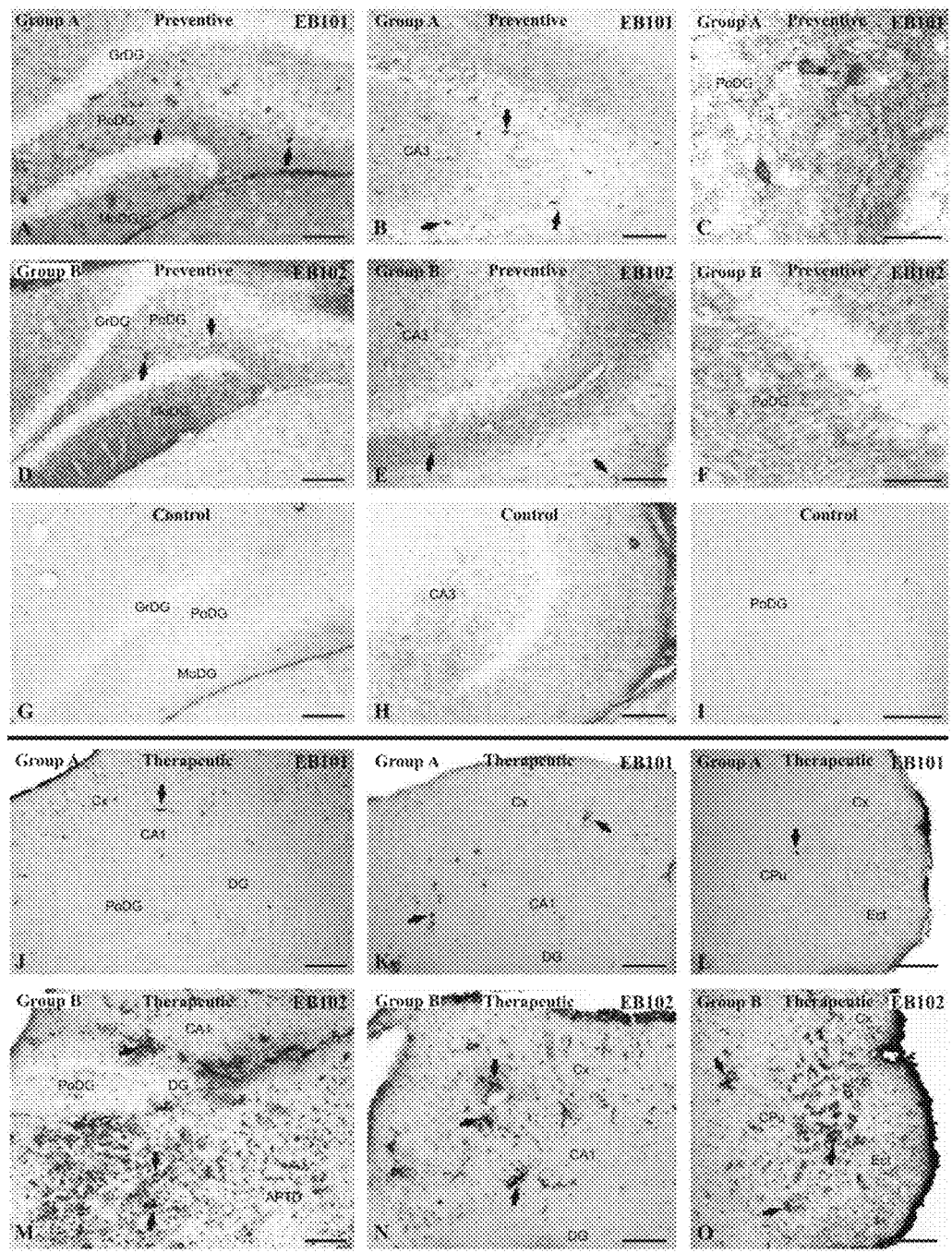
FIG. 19 shows that the EB101 vaccine increases B-cells in the brains of PS1/APP transgenic mice.

FIG. 19 shows that the EB101 vaccine increases B-cells in the brains of PS1/APP transgenic mice. FIG. 19 shows comparative photomicrographs of hippocampus and cortical brain regions at in the preventive (A-I; phase I) and therapeutic treatment (J-O; phase II) experimental periods, showing B-cell CD45RA immunoreactivity. A-I show transverse brain sections of 15-months-old mice from the prophylactic treatment period; mice immunized with EB101 show an abundant density of immunoreactive B-cells (A-C) when compared with mice treated with EB102 (D-F) and controls, group C (G-I). Note the an almost absence of immunoreactive B-cells in the wild-type brain sections (G-I), whereas the hippocampal sections of the EB101 immunized mice (A-C) shows a moderate immunoreactivity in response to the neuropathological inflammation inflammatory process. Photomicrographs J-O show transverse brain sections of 21-month-old mice treated with EB101 (group A), period, showing a moderate to scarce density of immunoreactive B-cells at the dentate gyrus (J) retrosplenial cortex/hippocampal subregion CA1 (K) and ectorhinal cortex (L) (group A), contrasting markedly with the massive immunoreactive density of B-cells observed in EB102 treated mice (M-O). Note the extensive response to the neuropathological inflammation process in brain sections of group B mice. Scale bar: 100 μm.

8. Synaptic Distribution in B6C3-Tg Transgenic Mice Brains

Comparing the cytoarchitecture and neuronal distribution of the synaptic marker synaptophysin in all mice brains, we have not observed significant differences or density variation among all the mice of the three groups (data not shown).

9. Apoptosis

Figure 12:
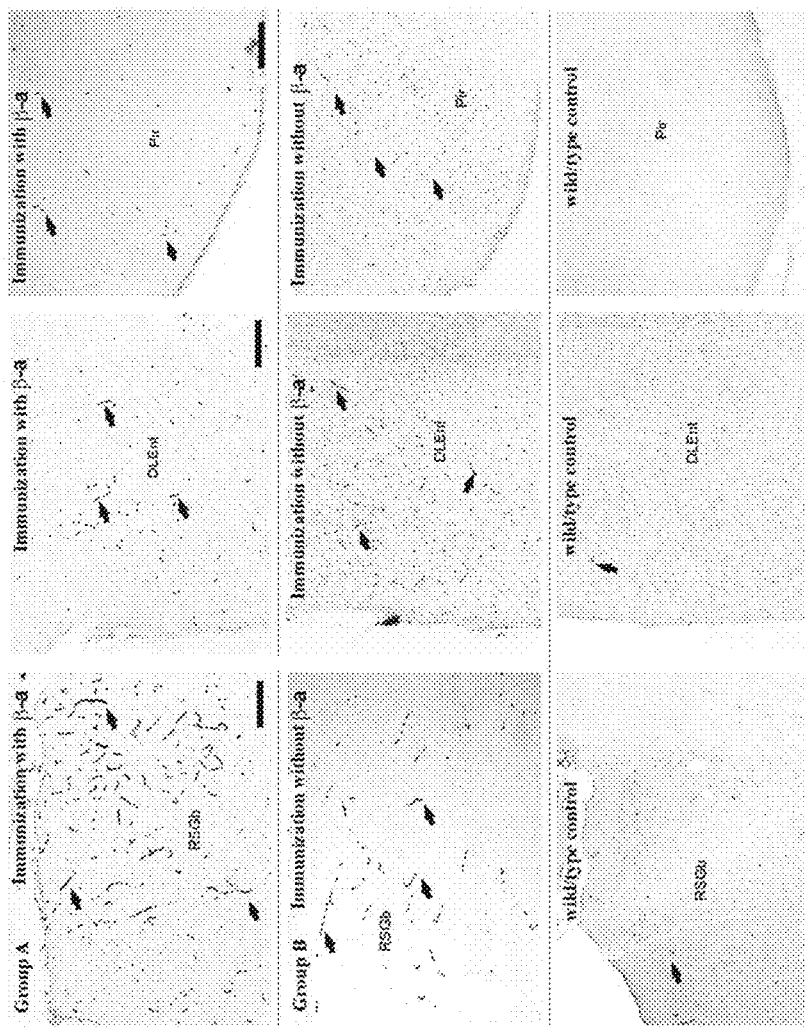
FIG. 12. shows that EB101-immunization reduces apoptosis in the brains of Tg(APP/PSEN)-AD mice. Comparative image of hippocampus and cortical regions showing significant apoptotic reduction in Aβ-treated mice after administration of EB101-immunization compared with that of mice treated with EB102(group B) or controls (group C). Note the normal levels of T-cells in the wild/type sections. Scale bars: 100 μm.

To examine the neuronal vulnerability and cell loss associated with AD pathology, we have performed apoptotic labeling experiments in the brain regions of all mice groups (FIG. 12). We have found numerous apoptotic structures in both immunized groups. Although mice treated with EB101 showed slightly more apoptotic structures in the dorsal cortex (retrosplenial cortex), the mice in group B showed more apoptotic density in all the other cortical and hippocampal structures (FIG. 12).

10. Analysis of Variance (ANOVA)

Analysis of variance was performed in 84 transverse sections [35 (Group A); 35 (Group B); 14 (group C)]

Measurement: Aβ-plaques density per brain section:

| | GROUP A | | | | | | |
|---|---|---|---|---|---|---|---|
| | M1TA10 | M4TA9 | M7TA9 | M15TA9 | M12TA9 | M10w/tA10 | M13w/tA10 |
| Brg - 0.94 mm | 73 | 96 | 107 | 85 | 87 | 0 | 0 |
| Brg - 1.34 mm | 63 | 92 | 100 | 91 | 98 | 0 | 0 |
| Brg - 1.70 mm | 80 | 100 | 105 | 104 | 96 | 0 | 0 |
| Brg - 2.30 mm | 61 | 93 | 100 | 93 | 105 | 0 | 0 |
| Brg - 2.70 mm | 60 | 82 | 95 | 95 | 109 | 0 | 0 |
| Brg - 3.64 mm | 85 | 85 | 92 | 94 | 96 | 0 | 0 |
| Brg - 4.60 mm | 60 | 86 | 83 | 99 | 103 | 0 | 0 |

| | GROUP B ( | | | | | | |
|---|---|---|---|---|---|---|---|
| | M2TB10 | M5TB10 | M8TB9 | M16TB9 | M14TB9 | M11w/tB10 | M17w/tB10 |
| Brg - 0.94 mm | 80 | 96 | 107 | 69 | 110 | 0 | 0 |
| Brg - 1.34 mm | 85 | 94 | 112 | 72 | 96 | 0 | 0 |
| Brg - 1.70 mm | 84 | 102 | 110 | 83 | 108 | 0 | 0 |
| Brg - 2.30 mm | 76 | 111 | 120 | 108 | 148 | 0 | 0 |
| Brg - 2.70 mm | 81 | 102 | 153 | 92 | 125 | 0 | 0 |
| Brg - 3.64 mm | 80 | 106 | 162 | 78 | 110 | 0 | 0 |
| Brg - 4.60 mm | 73 | 108 | 152 | 75 | 109 | 0 | 0 |

| GROUP C | | | |
|---|---|---|---|
| | M3TC7 | M9TC9 | M6w/tC9 |
| Brg - 0.94 mm | 96 | 115 | 0 |
| Brg - 1.34 mm | 103 | 112 | 0 |
| Brg - 1.70 mm | 100 | 128 | 0 |
| Brg - 2.30 mm | 104 | 120 | 0 |
| Brg - 2.70 mm | 96 | 124 | 0 |
| Brg - 3.64 mm | 92 | 116 | 0 |
| Brg - 4.60 mm | 87 | 104 | 0 |

One-Way ANOVA Hypothesis:

Ho: There are no differences among the three group means.

H1: There are significant differences among some or all of the individual means.

Differences among the three group means were determined by statistical tests analyzing the variance that yields a statistic F, which indicates if there is a significant difference among our three group means.

ANOVA analyses were performed to assess: Differences among groups (Variation between the means of the three "treatments" due to chance (random sampling error) and the effects, if any, of these treatments), and differences within each group (Variation due to chance (random sampling error) among individuals affected by the same treatment).

| Groups | n | Sum | Mean | Variance |
|---|---|---|---|---|
| Group A | 35 | 3153 | 90.085 | 178.904 |
| Group B | 35 | 3577 | 102.2 | 578.517 |
| Group C | 14 | 1497 | 106.928 | 155.302 |

Analysis of Variances:

| Origin of variances | Sum of squares | Degrees of freedom | Mean square | F | Probability | F Ratio |
|---|---|---|---|---|---|---|
| Among groups | 3925.431 | 2 | 1962.715 | 5.724 | 0.004 | 3.109 |
| Within each group | 27771.271 | 81 | 342.855 | | | |
| Total | 31696.702 | 83 | | | | |

Conclusion I: Since Fobs (5, 7) is > Fcrit (3.1) and P (0.004) is < α (0.05), the Ho is rejected and we conclude that there are significant differences among treatments.

Variances Between Groups:

| | Group 1 | Group 2 | Group 3 |
|---|---|---|---|
| Group A | 1 | | |
| Group B | 0.415 | 1 | |
| Group C | 0.697 | 0.808 | 1 |

Groups B and C resemble each other more closely.

Scheffe Test results (Comparisons among means of two groups):

F1-2=4,3
F1-3=4,13
F2-3=0,32
F(0.05) [2,81]=3.15

From the analysis of these data (F1-2=4,3 y F1-3=4,13 are>than the critical value of F(0.05)=3.15), we conclude that the treatment in group A had a statistically significant effect on the A. beta peptide burden.

The experiments described in this example show a dramatic effect of EB101 in the reduction of beta amyloid and neurofibrillary tangle burden, and in the reactive astrocytes, indicating an additional anti-inflammatory effect by EB101. Furthermore, the confocal images indicate the close relationship between all the neurodegenerative markers analyzed, suggesting their association during the pathological progression of AD. In these studies we showed also that non-Aβ-treated APP mice, groups B and C, presents an acute T-cell immunologic response when compared with the treated EB101 mice.

In previous reports from an early clinical study with A. beta peptide vaccine, AN1792, delivered in a classical adjuvant, a fatal meningoencephalitis-like reaction was reported in 6% of the patients treated, suggesting that a proinflammatory reaction was elicited by this vaccine formulation. Our present results suggest that such reaction may be caused by a T cell-mediated autoimmune response that builds up as this disease progresses and it probably was exacerbated by the AN1792 adjuvant used in their formulation. One preferred embodiment of the vaccine of this invention, EB101, prevents this exacerbated inflammatory reaction as shown by the reduced density in B and T immunoreactive cells in the hippocampus and cortical regions of these transgenic animals, suggesting that our choice of adjuvant might be ideal for delivery of A. amyloid peptide. EB101 dramatically reduced the neuronal pathology associated with AD, amyloid plaques and neurofibrillary tangles, and inhibited inflammatory reactions.

What is claimed is:

1. A method for treating Alzheimer's disease (AD) or AD-like Down syndrome, said method comprising: administering, to a patient in need thereof, a dose of a liposome formulation which contains between 10 and 50 µg of an Aβ1-42 amyloid-beta peptide, and between 0.1 and 10 µg of sphingosine-1-phosphate, said dose being an amount effective to induce the production of antibodies against the Aβ1-42 amyloid-beta peptide in said patient, wherein the said liposome formulation comprises 1,2-dioleoyl-sn-glycero-3-phosphocholine, l-palmitoyl-2-oleoyl-sn-glycero-3-phosphatidylglycerol, cholesterol and D-erythro-sphingosine-1-phosphate which are present at a molar ratio of 0.3:0.3:0.39:0.01, respectively.

2. The method of claim 1, wherein the patient is administered a dose of the liposome formulation which contains 10 µg of the Aβ1-42 amyloid-beta peptide, and approximately 6 µg of sphingosine-1-phosphate.

3. The method of claim 1, wherein a lipid component of said liposomes is pegylated.

4. The method of claim 1, wherein the Aβ1-42 amyloid-beta peptide is PEGylated.

5. The method of claim 1, wherein the sphingosine-1-phosphate is pegylated.

6. The method of claim 1, wherein the sphingosine-1-phosphate is bound to the Aβ1-42 amyloid-beta peptide, and bound to the liposome phospholipids.

7. The method of claim 1, wherein the patient is a human.

8. The method of claim 1, wherein the patient has not been assessed for the presence of amyloid deposits.

9. The method of claim 1, wherein the patient is younger than 50 years old.

10. The method of claim 1, wherein the patient has inherited risk factors indicating susceptibility to Alzheimer's disease.

11. The method of claim 1, wherein the patient has no known risk factors for Alzheimer's disease.

12. The method of claim 1, wherein the Aβ1-42 amyloid-beta peptide is administered in aggregated form in said liposomes.

13. The method of claim 1, wherein the Aβ1-42 amyloid-beta peptide is administered in nonaggregated form in said liposomes.

14. The method of claim 1, wherein the liposome formulation is administered orally, subcutaneously, intramuscularly, topically or intravenously.

15. The method of claim 1, wherein said liposomes are multilamellar liposomes.

16. The method of claim 1, wherein said liposomes are small lamellar liposomes.

17. The method of claim 1, wherein said liposomes are single lamellar or multilamellar liposomes.

18. The method of claim 1, wherein the sphingosine-1-phosphate is administered at a dose which does not induce an immune response against sphingosine-1-phosphate in said patient.

19. The method of claim 1, wherein the patient does not have inherited risk factors indicating susceptibility to Alzheimer's disease.

20. The method of claim 1, wherein the patient has known risk factors for Alzheimer's disease.

* * * * *